United States Patent [19]

Weiner et al.

[11] Patent Number: 6,036,957
[45] Date of Patent: *Mar. 14, 2000

[54] SUPPRESSION OF T-CELL PROLIFERATION USING PEPTIDE FRAGMENTS OF MYELIN BASIC PROTEIN

[75] Inventors: Howard L. Weiner, Brookline; David A. Hafler, West Newton, both of Mass.; Ariel Miller, Ahuza, Israel; Ahmad Al-Sabbagh, Norwood, Mass.

[73] Assignee: Autoimmune, Inc., Lexington, Mass.

[ * ] Notice: This patent is subject to a terminal disclaimer.

[21] Appl. No.: 08/469,640

[22] Filed: Jun. 6, 1995

Related U.S. Application Data

[60] Division of application No. 08/046,354, Apr. 9, 1993, abandoned, which is a continuation-in-part of application No. 07/865,318, Apr. 9, 1992, abandoned, which is a continuation-in-part of application No. 07/502,559, Mar. 30, 1990, abandoned, and a continuation-in-part of application No. 07/843,752, Feb. 28, 1992, abandoned.

[51] Int. Cl.[7] .......................... A61K 39/00; A61K 38/17; C07K 7/08; C07K 14/47
[52] U.S. Cl. .......................... 424/184.1; 514/12; 514/13; 530/300; 530/324; 530/325; 530/326
[58] Field of Search .................. 424/184.1; 530/300, 530/350, 324, 325, 326; 514/12, 13

[56] References Cited

U.S. PATENT DOCUMENTS 4,634,590  1/1987  Cohen et al. ............................ 424/88

FOREIGN PATENT DOCUMENTS

| 0 304 279 A2 | 2/1989 | European Pat. Off. . |
| 0 271 577 B1 | 10/1995 | European Pat. Off. . |
| WO 80/02501 | 11/1980 | WIPO . |
| WO 95/31990 | 11/1995 | WIPO . |

OTHER PUBLICATIONS

Driscoll et al J immunology vol. 117 No. 1 110, Jul. 1976.
Swanborg J Immunology vol. 114 No. 1 Part 1 191, Jan. 1975.
Martenson J Neurochemistry vol. 40 951, 1983.
Richert et al Annals New York Acad Sci vol. 540 345, 1988.
Richert et al Annal Neurology vol. 26(3) 32, Sep. 1989.
Rujinami et al Science vol. 230:1043–45, 1985.
Uyemura et al J Neurobiology vol. 39:895, 1982.
Hruby et al J Neurochem vol. 44:637, 1985.
Jahnke et al Science vol. 229:282, 1985.
Higgins et al J Immunology vol. 140 No. 2 440, Jan. 1988.
Michael, J.G. Immunological Investigations vol. 18 (9&10) 1049, 1989.
Fridkis–Hareli et al., *Proc. Natl. Acad. Sci.*, 91:4872–4876, May 1994.
Rudick, R.A. *NEJM*, 337: 1604, 1997.
Higgins et al., *J. Immunology*, 140:440–445, 1988.
Eylar, *Adv. Exp. Med. Bio.*, 98:259–281, 1978.
Sriram et al., *Cell. Immunol.*, 75:378–382, 1983.
Nagler–Anderson et al., *PNAS*, 83:7443–7446, 1986.
Schoen, *J. Immunol.*, 128:717–719, 1982.
Higgins et al., *Annals Neurology*, abstract No. P154, 1986.
Whitacre et al., *6th Int'l. Cong. Immunol.*, abstract No. 3.62.21, 1986.
Zamvil et al., *Nature*, 324:258–260, 1986.
Fritz et al., *J. Immunol.*, 134:2328–2332, 1985.
Fritz et al., *J. Immunol.*, 130:191–194, 1983.
Pettinelli et al., *J. Immunol.*, 129:1209–1211, 1982.
Whitaker et al., *J. Bio. Chem*, 250:9106–9111, 1975.
Thompson et al., *Clin. Exp. Immunol.*, 64:581–586, 1985.
Lider et al., *J. Immunol.*, 142:748–752, 1989.
Friedman et al., *PNAS*, 91:6688–6692, 1994.
Adorini et al., *Nature 342*:800–2, 1989.
Allegretta, M., et al., *Science*, 247:718–721, 1990.
Avrilionis, K. and Boggs, J.M., *J. Neuroimmunol.* 35:201–10, 1991.
Ben–Nun, A., et al., *J. Immunol.*, 129:303–308, 1982.
Blackman et al., *Science 248*:1335–41, 1990.
Burns, F.R., et al., *J. Exp. Med.*, 169:27–39, 1989.
Buss et al., *Cell 47*:1071–77, 1988.
Cresswell, *Nature 343*:593–94, 1990.
DeFreitas et al., *Proc. Natl. Acad. Sci. USA 83*:2637–41, 1986.
Gaur et al., *Science 258*:1491–4, 1992.
Germain, *Nature 344*:19–22, 1990.
Guillet et al., *Nature 324*:260–62, 1986.
Guillet et al., *Science 235*:865–70, 1987.
Hodes et al., *Science 246*:1041–44, 1989.
Howell, M.D., et al., *Science*, 246:668–670, 1989.
Janeway, *Nature 341*:482–83, 1989.
Kaye et al., *Nature 341*:746–49, 1989.
Lider et al., *Ann. N. Y. Acad. Sci.*, pp. 267–273, 1986.
MacDonald, *Science 246*:982, 1989.
Martin, R., et al., *J. Immunol. 145*:540–8, 1990.
Martin, R., et al., *J. of Exper. Med. 173*:19–24, 1991.
Martin, R., et al., *J. Immunol. 148*:1359–1366, 1992.
Mokhtarian, F., et al., *Nature*, 309:356–358, 1984.
Nikolic–Zugic et al., *Nature 344*:65–67, 1990.
Ogasawara et al., *Nature 325*:450–52, 1987.
Oksenberg et al., *Nature 345*:344–46, 1990.
Ota, K, et al., *Nature*, 346:183–7, 1990.
Pette, M., et al., *Proc. Natl. Acad. Sci., USA 87*:7968–72, 1990.
Schwartz, *Ann. Rev. Immunol. 3*:237–61, 1985.
Su, X., et al., *J. Neuroimmunol. 34*:181–190, 1991.
Vandenbark, A.A., et al., *Nature*, 341:541–433, 1989.
Weiner et at., (Abstr) *Neurology* (Suppl. 1) 39:172, 1989.
Wucherpfenning, K.W. et al., *Science 248*:1016–9, 1990.
Zamvil, S. S., et al., *Nature*, 324:258–260, 1986.
Bitar, dissertation entitled, *The Suppressive Effects of Oral Myelin Basic Protein . . .* , 1986.

(List continued on next page.)

*Primary Examiner*—Julie Burke
*Attorney, Agent, or Firm*—Darby & Darby

[57] ABSTRACT

Peptides are administered to individuals suffering from multiple sclerosis. The peptides contain immunodominant epitopes of myelin basic protein that are recognized by T-cells from relapsing-remitting multiple sclerosis patients, and that are contained in the 84–102 and 143–168 regions of human MBP.

5 Claims, 12 Drawing Sheets

OTHER PUBLICATIONS

Nagler–Anderson, dissertation entitled, *Immunoregulation of an Exp. Model of Autoimmunity*, 1986.
Rothbart, *1st Forum in Virology*, pp. 518–520, 1986.
Bitar et al., *Cell. Immunol.*, 112:364–370, 1988.
Eylar et al., *Neurochem. Research*, 4:249–258, 1979.
Kagnoff, *Oral Tolerance*, pp. 248–269, 1982.
Mowat, *Immunol. Today*, 8:93–98, 1987.
Weiner et al., *Science*, 259:1321–1324, 1993.
Campbell et al, *Arch. Neurol.*, 29:10–15, 1973.
Carnegie et al.,*Immunol.* 19:55–63, 1970.
Fritz et al., *J. Immunol.*, 130:1024–1026, 1983.
Hashim et al., *Arch. Biochem. and Biophy.*, 156:287–297, 1973.

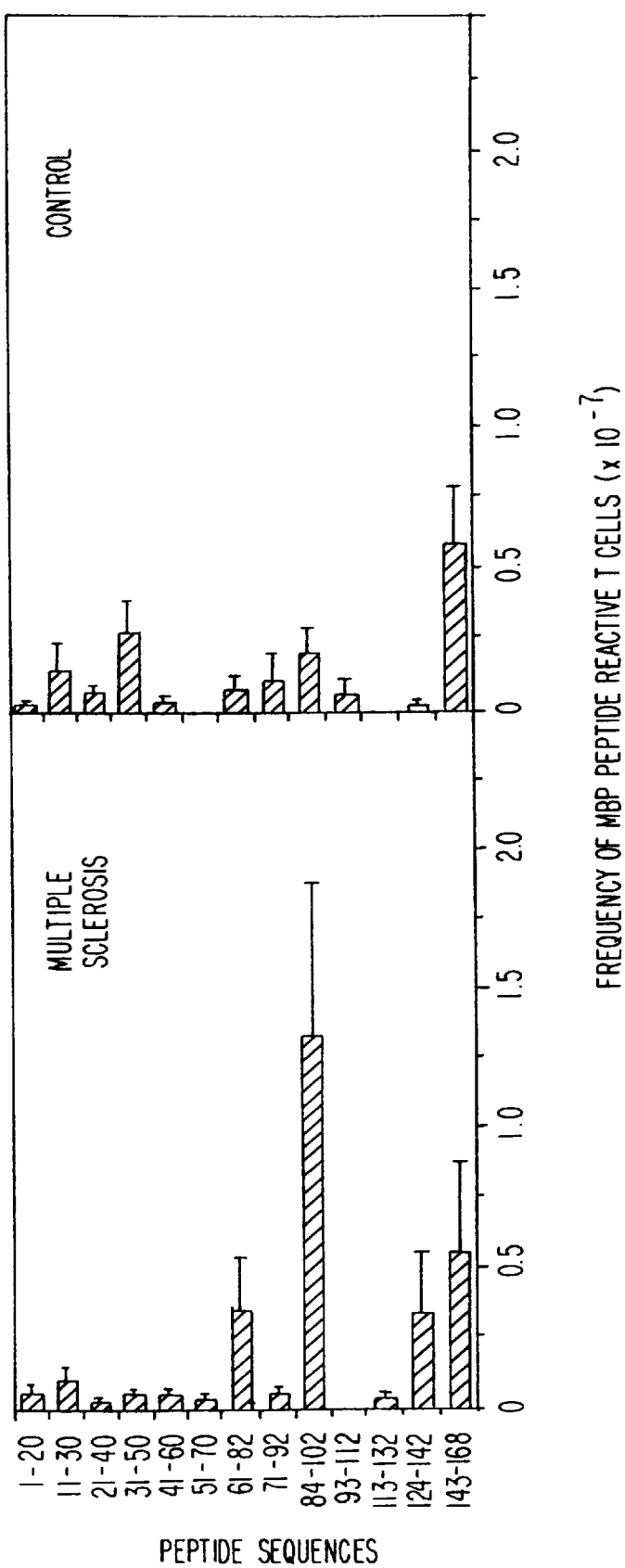

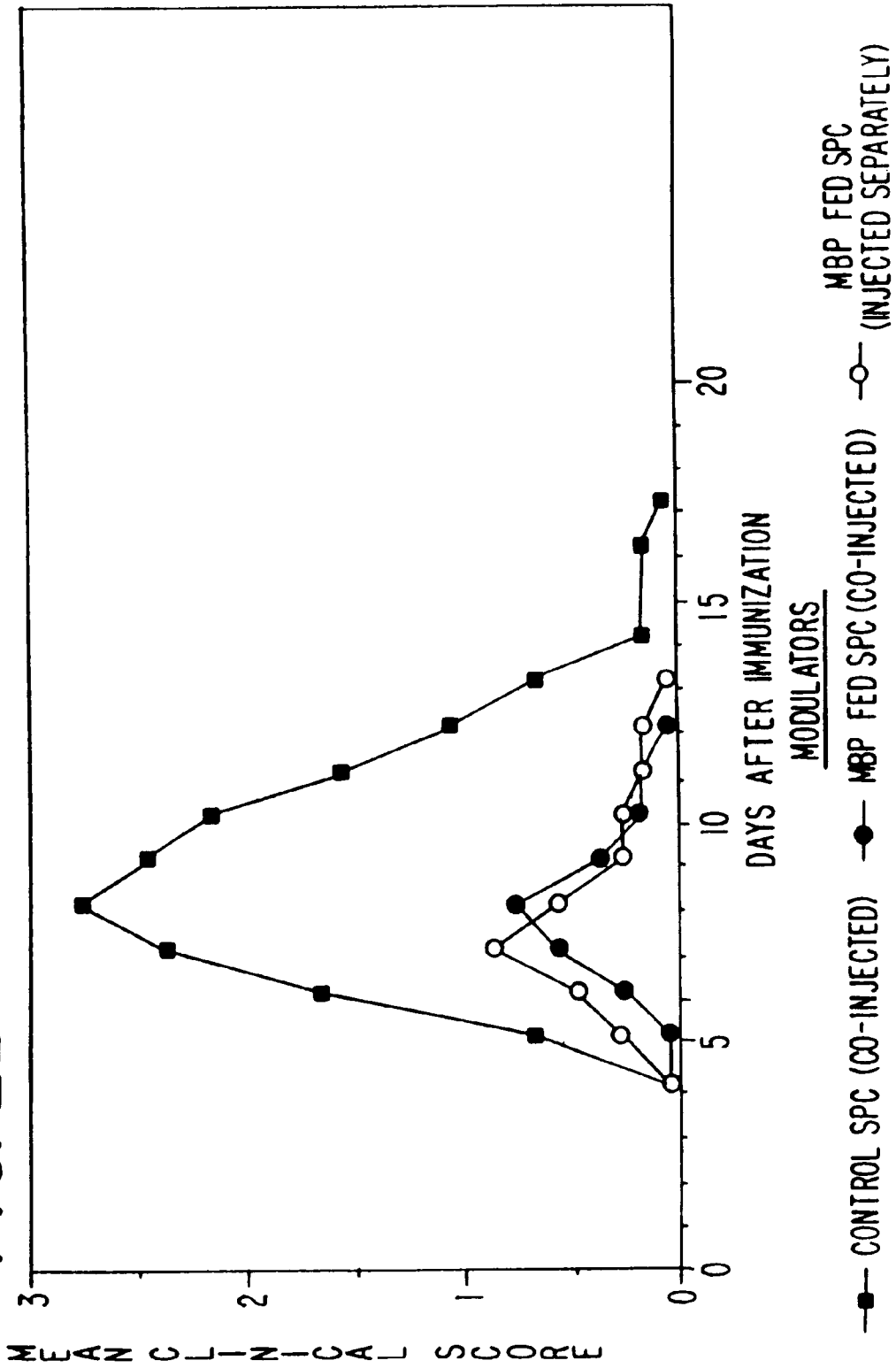

| Binding to DRB1*1501 nM | MBP 85-99 | Sequence | HY.2E11 | OB.1A12 | OB.2F3 | OB.1H8 | OB.1C3 |
|---|---|---|---|---|---|---|---|
| 1.1 | (85A) | ANPVVHFFKNIVTPR | >90% | >90% | >90% | >90% | >10% |
| 3.1 | (86A) | EAPVVHFFKNIVTPR | >90% | >90% | >90% | >90% | >90% |
| 3.7 | (87A) | ENAVVHFFKNIVTPR | >90% | >90% | >90% | >10% | — |
| 1.4 | (88A) | ENPAVHFFKNIVTPR | >90% | >90% | >10% | >10% | — |
| 170 | (89A) | ENPVAHFFKNIVTPR | >90% | — | — | — | — |
| 1.9 | (90A) | ENPVVAFFKNIVTPR | >90% | — | — | — | — |
| 9.3 | (91A) | ENPVVHAFKNIVTPR | — | — | — | — | — |
| 370 | (92A) | ENPVVHFAKNIVTPR | >90% | >90% | — | >10% | >10% |
| 4.1 | (93A) | ENPVVHFFANIVTPR | — | >90% | — | — | — |
| 4.5 | (94A) | ENPVVHFFKAIVTPR | >90% | >90% | >90% | >90% | >90% |
| 3.2 | (95A) | ENPVVHFFKNAVTPR | >90% | >90% | >90% | >90% | >90% |
| 3.0 | (96A) | ENPVVHFFKNIATPR | >90% | >90% | >90% | >90% | >90% |
| 0.55 | (97A) | ENPVVHFFKNIVAPR | >90% | >90% | >90% | >90% | >90% |
| 0.69 | (98A) | ENPVVHFFKNIVTAR | >90% | >90% | >90% | >90% | >90% |
| 1.0 | (99A) | ENPVVHFFKNIVTPA | >90% | >90% | >90% | >90% | >90% |
| 4.3 | (NONE) | ENPVVHFFKNIVTPR | >90% | >90% | >90% | >90% | >90% |

T CELL CLONES $^3$H - THYMIDINE UPTAKE COMPARED TO NATIVE PEPTIDE

>90% MAXIMUM STIMULATION
>10% MAXIMUM STIMULATION
50% MAXIMUM STIMULATION
NO ACTIVITY

FIG. 11

SUPPRESSION OF T-CELL PROLIFERATION USING PEPTIDE FRAGMENTS OF MYELIN BASIC PROTEIN

This is a division, of application Ser. No. 08/046,354, filed Apr. 9, 1993, now abandoned which is a continuation-in-part of (i) U.S. application Ser. No. 07/865,318, filed Apr. 9, 1992 now abandoned, which is a continuation-in-part of U. S. application Ser. No. 07/502,559, filed Mar. 30, 1990 now abandoned; and (ii) Ser. No. 07/843,752, filed Feb. 28, 1992 now abandoned.

The United States Government has rights to this invention by virtue of funding from Grant Nos. NS 24247 and NS 29352 both from the National Institutes of Health.

FIELD OF THE INVENTION

This invention pertains to compositions and methods for suppression of T-cell mediated or T-cell dependent autoimmune response. More specifically, the invention is directed to compositions comprising peptide fragments of myelin basic protein (MBP) or analogs thereof, and to methods of using such peptides and compositions to anergize, or to stop proliferation of, human T-cells specific for myelin basic protein, or to elicit active suppression of such T-cells. Peptides according to the invention are also useful in identifying $CD4^+$ T-cells reactive with myelin basic protein.

BACKGROUND OF THE INVENTION

The discussion in this section is not limited to discussion of work that qualifies as "prior art" against the present invention. Therefore, no such admission and no declaration against the present inventors' interests shall be implied by reason of this discussion.

Multiple Sclerosis (MS) is a chronic inflammatory disease of the white matter of the human central nervous system and is believed to be of autoimmune etiology. Regardless of its etiology, MS is accompanied by autoimmune attack of nerve tissue. For example, the disease is characterized by prominent T-cell and macrophage infiltrates into nervous tissue (i.e., the brain, spinal cord, peripheral nerves or associated cell types), demyelination and neurological dysfunction. Myelin basic protein (MBP) has been extensively studied by the present inventors, their co-workers and others as an autoantigen in the disease because of its role as an inducing agent in the major animal model of MS, experimental allergic encephalomyelitis (EAE), as well as its role in the human disease post-viral encephalomyelitis. In addition, the present inventors and their co-workers have studied MBP as a "bystander antigen" (Serial No. 843,752, supra).

A major hypothesis regarding the pathogenesis of MS is that T-cells reactive with myelin basic protein in the white matter of the CNS initiate the inflammatory process. Another hypothesis is that T-cells reactive with proteolipid protein (PLP) initiate the inflammatory process. The demonstration that activated T-cells specific for myelin basic protein (MBP) can be isolated from MS patients (Allegretta, M., et al., *Science*: 247: 778, 1990) further implicates MBP-reactive T-cells in the pathogenesis of the disease. The work of the present inventors also shows that MBP-reactive T-cells are involved in the pathology of the disease, subsequent to initiation of the inflammatory process. (As will be described in more detail below, the present inventors demonstrated that healthy individu- als also often have MBP-specific T-cells, but unlike those of MS patients, MBP-specific T-cells from healthy individuals are not activated.)

The current treatments for MS are solely palliative and involve administration of drugs which act in a non-specific fashion to suppress the immune response in the subject. Examples of such drugs are cyclophosphamide, Imuran (azathioprine) and Cyclosporin A. Steroid compounds such as prednisone and methylprednisolone are also employed in many instances. These drugs have limited efficacy against MS. Use of such drugs is limited by their toxicity and by the fact that they induce "global" immunosuppression upon prolonged use, i.e., they also down-regulate the normal protective immune response to pathogenic microorganisms thereby increasing the risk of infection. In addition, patients that are globally immunosuppressed for prolonged periods of time run an increased risk of developing certain malignancies.

More details on the immunological processes occurring are known for experimental allergic encephalomyelitis (EAE), the primary animal model for MS. EAE can readily be induced in small mammals by immunization with myelin basic protein (MBP) in an appropriate adjuvant or by adoptive transfer through the injection of $CD4^+$, MBP-reactive T-cells (Alvord Jr, E. C., et al. eds. in *Experimental Allergic Encephalomyelitis: A Useful Model for Multiple Sclerosis*, A. R. Liss, N.Y., 1984; Makhtarian, D. E., et al. *Nature* 305:356, 1984; Ben-Nun, A. et al. *J. Immunol.* 129:303, 1982). The T-cells that induce EAE in both mice and rats, termed encephalitogenic cells, specifically recognize peptides corresponding to the immunodominant regions of MBP. The presentation of these regions to the T-cells occurs on the surface of antigen-presenting cells (APCs) in association with unique Major Histocompatibility Complex (MHC) class II molecules. It should be emphasized that immunodominant regions of MBP, that is the portion of the protein most often recognized by MBP-reactive T-cells of the CD4+ type, differs depending on the species of the host mammal and may also differ depending on the species of MBP, despite the fact that the amino acid sequence of MBP exhibits very high interspecies homology. For example, as the present inventors and their co-workers have discovered, an immunodominant epitope of human MBP in humans is contained within the subsequence of the human MBP molecule comprising amino acids 84–102. Another immunodominant epitope can be found in the subsequence of the human MS molecule comprising amino acids 143–168. This is evidenced by the specificity of human T-cells isolated from individuals afflicted with MS (related patent application Ser. No. 502,559 and Example 1 below). The immunodominant region of mouse MBP is amino acids 1–9 when administered to mice (Zamvil et al., *Nature* 324:258, 1986) and that of rat MBP is amino acids 68–88 when administered to rats (Burns et al., *J. Exp. Med.* 169:27, 1989). On the other hand, the immunodominant region of guinea-pig MBP in rats is located within residues 75–84 (Hashim, G. Myelin: Chemistry and Biology, Alan R. Liss, N.Y. 1980).

Based on the work done in the EAE system, alternative therapies are being developed for the treatment of autoimmune diseases in general and MS in particular. U.S. patent application Ser. No. 65,794 filed Jun. 24, 1987 (now abandoned) and co-pending International Patent Application PCT/US88/02139, filed Jun. 24, 1988, corresponding to national stage United States application Ser. No. 07/460, 852, now abandoned and a continuation-in-part of this application, U.S. application Ser. No. 07/596,936, now abandoned disclose that oral or enteral administration of whole myelin basic protein as well as disease-inducing and non-inducing fragments and analogs thereof is effective in suppressing acute monophasic EAE and are useful in suppressing MS symptoms when similarly administered.

The following co-pending commonly assigned patent applications are also of interest: U.S. patent application Ser.

No. 454,806 filed Dec. 20, 1989, now abandoned discloses the aerosol administration of autoantigens, disease-suppressive fragments of said autoantigens and analogs thereof as an effective treatment for treating T-cell mediated autoimmune diseases such as MS.

U.S. application Ser. No. 07/487,732, filed Mar. 20, 1990, now abandoned entitled "Enhancement of the Down Regulation of Autoimmune Diseases by Oral Administration of Autoantigens" discloses synergists (enhancers) for use with oral administration of autoantigens, disease-suppressive fragments and analogs thereof as effective treatments for T-cell mediated autoimmune diseases.

U.S. application Ser. No. 07/843,752, now abandoned discloses methods and compositions for treating autoimmune diseases orally or by inhalation by administering bystander antigens. Bystander antigens are tissue-specific antigens that are present at the locus of autoimmune attack and that have the ability upon their being orally administered to generate T-suppressor cells which in turn suppress immune attack at the afflicted tissue. Bystander antigens are not necessarily autoantigens and are not necessarily themselves the target of immune attack. (In fact, there is evidence that the immunosuppressive epitope(s) of an autoantigen are different from the immunodominant epitope(s) thereof, although immunodominant epitopes (which do elicit suppression upon oral administration) may act as bystander antigens in suppressing immune attack directed against other portions of the same antigen or portions of other antigens in the afflicted tissue.) However, bystander antigens must (a) be specific to the afflicted tissue and (b) possess the ability to elicit T-suppressor cells upon oral administration.

It has now been found that oral administration of multiple doses and small amounts of whole antigens containing encephalitogenic immunodominant epitopes elicits this type of active suppression. On the other hand, i.v. administration of entire autoantigen (or of one or more encephalitogenic immunodominant epitope-containing fragments thereof) also induces suppression but only of immune attack T-cells recognizing epitopes of the autoantigen. The latter type of suppression, which is believed to proceed via the mechanism of clonal anergy, is also observed upon oral administration of single doses and large amounts of antigens encompassing encephalitogenic epitopes, specifically immunodominant epitopes, especially when such antigens are accompanied by protease inhibitors.

For human MBP, a protein believed to be an autoantigen for MS, extensive testing by the present inventors has revealed fragments of the protein incorporating epitopes which are recognized by a large number of MBP-specific immune attack (CD4$^+$) T-cells isolated from MS patients. Such fragments, comprising immunodominant epitopes, are likely candidates for administration to patients suffering from MS, with the goal of suppressing autoimmune response, and particularly suppressing the function of MBP-reactive T-cells that are responsible for autoimmune attack on nervous tissue. To that end, the present invention contemplates not only oral administration of such peptide fragments to mammals in need for such treatment but also parenteral administration of such fragments.

Therefore, it is an object of the present invention to provide immune-suppressive agents, specifically fragments of human MBP, and methods of using these fragments to suppress human T-cell functions.

Another object of the present invention is to provide compositions and pharmaceutical formulations comprising these fragments of human MBP useful for oral and/or i.v. administration to humans, and methods of use of such formulations.

Yet another object of this invention is to provide, as a reagent that could be used to determine the specificity of human T-cells, a peptide fragment of MBP incorporating an immunodominant epitope.

A further object is to provide compounds and compositions that anergize MBP-reactive T-cells or cause active suppression of such T-cells, the latter being evidenced for example by suppression of proliferation of MBP-reactive T-cells.

These and other objects of the present invention will be apparent to those of ordinary skill in the art in light of the present specification, drawings and claims.

BRIEF DESCRIPTION OF THE DRAWINGS

FIG. 1 is a bar graph showing the frequency of MBP reactive T-cells isolated from MS patients (left panel, FIG. 1A) and healthy controls (right panel, FIG. 1B) that react specifically with different human MBP peptide fragments.

FIG. 6, in graph B, depicts the effect on adoptively transferred EAE of IV administration of MBP and the inability of spleen cells of IV-tolerized animals to confer suppression when they are co-transferred to naive animals along with an encephalitogenic MBP line.

FIG. 11 is a chart showing the induction of proliferation of T-cell clones to the human 85–99 MBP peptides of the present invention as compared to the proliferation induced in these clones by the native MBP protein.

SUMMARY OF THE INVENTION

Figure 2A:
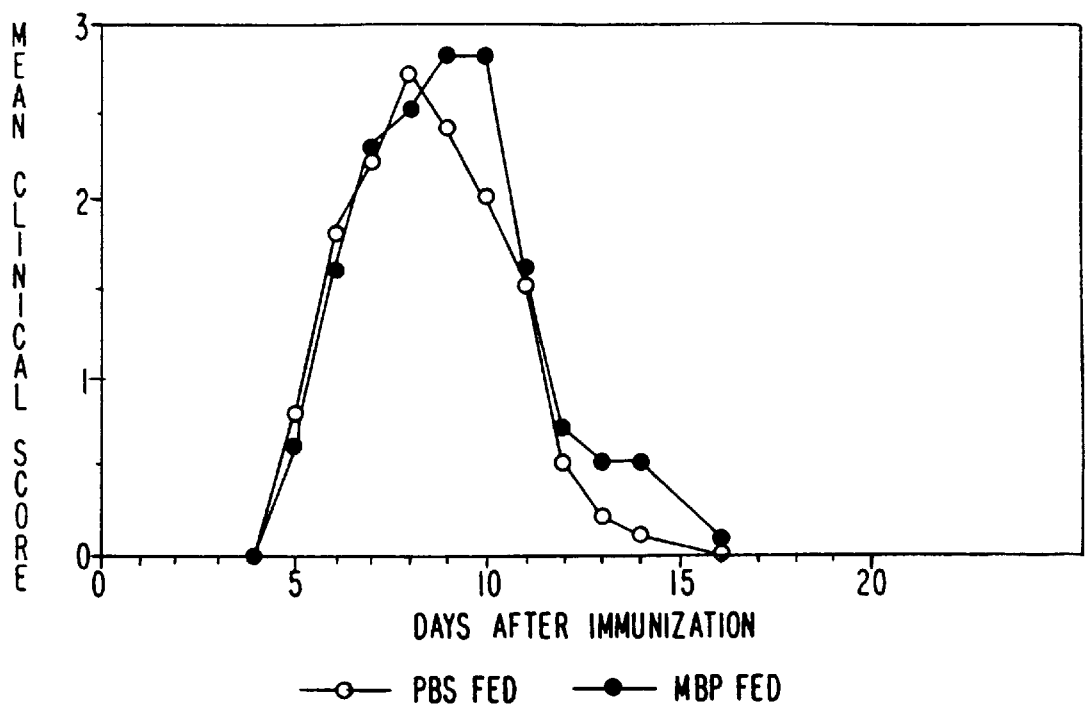
FIG. 2 graphically illustrates the suppression of EAE (induced by i.p. inoculation with MBP-specific encephalitogenic T-cells) by transfer of spleen cells from animals orally tolerized with MBP.

In one aspect, this invention is directed to immunosuppressive agents comprising peptides which are fragments of human MBP. Embodiments of the invention include peptides and pharmaceutical compositions comprising these peptides.

This invention is also directed to methods using the foregoing peptides to suppress immune response against myelin basic protein and tissues containing it, and/or to suppress T-cells that recognize an immunodominant epitope of human MBP. These methods involve oral and/or parenteral administration of one or more peptides according to the invention, and result in suppression of the immune response against the protein and tissues containing it.

Also included in the present invention are fragments of human MBP comprising the amino acid sequence ENPVVHFFKNIVTPR.

In a further aspect, the present invention is directed to pharmaceutical compositions comprising one or more of said fragments of MBP.

Additional aspects of the present invention involve methods of use of fragments of human MBP in the suppression of human T-cell function, and in the identification of $CD4^+$ MBP-reactive human T-cells.

DETAILED DESCRIPTION OF THE INVENTION

All patent applications, patents and publications cited in this specification are hereby incorporated by reference in their entirety. In the case of inconsistencies, the present disclosure, including definitions, will prevail.

As used herein, "suppression" includes any measurable reproducible reduction in T-cell proliferation in response to factors that normally stimulate those cells. However, it should be emphasized that the present invention is concerned only with the suppression of proliferation of deleterious T-cells, that is proliferation of T-cells that promote autoimmune attack ($CD4^+$ T-cells specific to a self-antigen, e.g. MBP). Indeed, an important aspect of the present invention is the ability to induce suppression in a restricted manner, where the suppression of deleterious T-cells specific to a self antigen is the result of choice of the fragment or fragments of MBP administered and/or the method of administration, as discussed below.

Suppression of the deleterious T-cell proliferation can also be measured indirectly, i.e. as seen through a reduction in symptoms of a disease which are directly or indirectly caused by immune attack T-cell proliferation, such as the damage to neural tissue observed in MS, or the decrease in the number or severity of attacks of MS suffered by MS patients. Damage to neural tissue can be assessed for example by magnetic resonance imaging (MRI) and measurement of the number and severity of lesions visible therein. Reduction in MS attack number or severity can be assessed for example by clinical evaluation of patients. Methods for both MRI and clinical evaluation are well-known in the art.

The term "autoantigen" is defined as any substance normally found within a mammal that, in an abnormal situation, is no longer recognized as "self" by the lymphocytes or antibodies of that mammal, and is attacked by the immunoregulatory system as though it were a foreign substance. In other words, an autoantigen is an antigen that is subject to autoimmune destruction. The mere presence of antibodies or even T-cells (of the $CD4^+$ type) specific to a native antigen does not establish it as an autoantigen. MBP and PLP (proteolipid protein) are examples of autoantigens in MS.

"Immunodominant epitope" of an autoantigen (such as MBP) means an antigenic determinant recognized by a substantial number including but not limited to a majority (although not necessarily an absolute majority) of T-cells of a sensitive mammal to which autoantigen such T-cells will mount or help mount an immune response if the sensitive mammal is also an afflicted mammal. (It is evident from this discussion that a "sensitive" mammal need not be an afflicted mammal.)

"Immunodominant regions" or "immunodominant domains" of an autoantigen are defined herein as those regions of the amino acid sequence of such autoantigen containing an immunodominant epitope. The structures (and/or location within the MBP or other autoantigen molecule) of immunodominant epitopes (and regions) of MBP or other autoantigen vary depending on the host and are, therefore, host-specific. The present inventors have in fact adduced evidence that the reason the immunodominant epitopes are host-specific is that they must comprise a motif (believed to be contained within a peptide fragment of about 8 to about 15 amino acids in length) that binds to the major histocompatibility complex of the host. This motif varies among different species (the MHC likewise varies) and may also exhibit polymorphism among members of the same species.

The term "analog" of fragments of MBP includes compounds that are so structurally related to the fragment of MBP that they possess the same biological activity as the MBP fragment. The biological activity referred to in this definition is the ability to suppress a T-cell mediated or T-cell dependent autoimmune response upon administration of the MBP fragment, or alternatively the ability to suppress proliferation of T-cells responsible for or contributing to autoimmune attack, or the ability to be recognized by T-cells recognizing an immunodominant epitope of MBP. An example of an analog of the fragment MBP 84–102 is the fragment MBP 84–102tyr, wherein amino acid 102 has been changed to tyrosine. As can be seen from FIG. 8, this change has little or no effect on the ability of the MBP fragment to stimulate proliferation of the MBP-reactive T-cell line. Furthermore, amino acid substitutions are not expected to have any effect on solubility or pharmacokinetics of a fragment because of the relatively small size of the present fragments. It should be noted that an "analog" need not display the same activity to the same degree, e.g., an "analog" does not need to be as potent a suppressor as an actual fragment of the native antigen.

Other analogs of the relevant human MBP epitopes could be constructed based on ability of these analogs to bind the MHC and to be recognized by the relevant T-cell receptor (both of which can be tested in vitro).

As used herein, "T-cells" or "T-lymphocytes" are defined as immune system cells, derived from stem cells located within hematopoietic (i.e. blood forming) tissues. There are three broad categories of T-cells: Helper, Suppressor and Cytotoxic. T-cells express either the CD4 antigen (and are then termed $CD4^+$ T-cells) or the CD8 antigen (in which case they are termed $CD8^+$ T-cells) on their cell surface. The expression of CD4 or CD8 antigens by peripheral (circulating) T-cells correlates with the function and specificity of the T-cell. "Helper T-cells" which are $CD4^+$ recognize antigens and Class II MHC molecules and perform helper or regulatory functions. "Cytotoxic" and "suppressor" T-cells (which are $CD8^+$) recognize antigens and Class I MHC molecules and perform cytotoxic and suppressor functions.

"Active suppression" is the suppression of immune function where the suppression is the result of the induction of additional immune cells, specifically, regulatory (suppressor) T-cells.

"Clonal anergy" is the suppression of immune function by induction in immune cells, specifically immune attack T-cells, of a state of unresponsiveness and more particularly unresponsiveness to presentation of the antigen to which these cells are normally specific and to which they would normally proliferate. 35 La Salle, J. et al, *J. Exp. Med.*, 176:177–186, July 1992. Anergized T-cells appear normal in all respects except they seem to be "turned off". They are not activated and—in the absence of added interleukin-2 (IL-2)—they do not proliferate on presentation of the antigen which they recognize. If IL-2 is added, the cells become de-anergized and begin to proliferate on presentation of antigen.

T-cells initiate an immune response when they encounter antigen-presenting cells (APCs), such as mononuclear phagocytes (macrophages, monocytes), Langerhan's cells or follicular dendritic cells, which initially take up, process (digest) and present antigenic fragments of a protein on their cell surface (in connection with their MHC). $CD4^+$ T-cells recognize antigen molecules exclusively when the protein is processed, and peptide fragments thereof are presented, by APCs that express Class II MHC molecules.

T-cell recognition of an antigen reflects a trimolecular interaction between the T-cell receptor (TCR), the MHC molecule of the APC and a peptide or peptides processed by the APC via a cleft or pocket in the three-dimensional structure of the Class II MHC molecule. (Bjorkman, P. J., et al., 1987, *Nature*, 329:506 and 329:512). The portion of the protein most often presented on the APC surface, and recognized by the T-cell is the immunodominant epitope.

The present inventors have identified two regions of human MBP which contain immunodominant epitopes of human MBP in a human host. These epitopes are resident within two distinct portions of the human MBP amino acid sequence (residues Nos. 82–104 and 143–168 respectively). As shown in Example 1 below, the present inventors have identified human MBP amino acid residues Nos. 84–102 as one immunodominant domain of human MBP recognized by a majority of peripheral T-cells isolated from patients suffering from MS. Additional experimentation has determined that the immunodominant epitope within this domain is further localized within human MBP amino acids Nos. 85–99. These data are presented in Example 3. (It appears by inference from the data in Example 3, that the minimal human MBP fragment within which the foregoing human host immunodominant epitope may reside is fragment 87–98 for some T-cell clones. But all T-cell clones reactive with 84–102 recognize the fragment 85–99.) A similar experiment with MBP fragment 143–168 can lead readily to identification of the precise locus of that immunodominant epitope.

Experiments involving the animal model of MS, EAE, have shown that protein fragments including corresponding immunodominant epitopes of guinea pig MBP and bovine MBP in rats, when administered orally to animals suffering from the disease, are effective in the suppression of the symptoms of the disease (related patent application Ser. No. 07/596,936 and Example 2 below) although some noninducing fragments are more potent suppressors than inducing fragments. Further, it has been shown that this orally effected suppression is due to the induction of $CD8^+$ suppressor T-cells (Lider et al., *J. of Immunol.* 142:748, 1989).

Some experiments have been conducted by others in animals using encephalitogenic fragments of MBP: See, e.g., Swierkosz, J. E., 1977, *J. Immunol.* 119:1501–1506; Su, X-M et al., 1991, *J. Neuroimmunol.* 34:181–190 (i.v. use of MBP fragments—determined to be encephalitogenic in mice—coupled to spleen cells to abate adoptively transferred EAE in mice); Avrilionis, K. et al., 1991, *J. Neuroimmunol.* 35:201–210 (i.v. use in guinea pigs of liposome-bound human MBP peptide fragment—shown to be encephalitogenic when administered to guinea pig—to suppress EAE induced with the same fragment and i.p. and s.c. use of the free peptide for the same purpose).

Thus, the peptides of the present invention can be advantageously used in the design of specific immunosuppressive preparations containing such peptides which are in turn useful for the suppression of deleterious T-cell proliferation. For example, peptides comprising sequences of the human MBP shown to induce anergy in human MBP-specific $CD4^+$ T-cells or to induce T-suppressor cells specific for demyelination can be constructed and used for such purposes. See, e.g., Examples 1 and 2 below. Further, the results reported in Example 2 indicate that the method and protocol of administration of the tolerizing agents affect the mechanism which brings about the suppression of the autoimmune reaction. Thus, peptide fragments incorporating an immunodominant epitope of human MBP in humans are effective in inhibiting proliferation of MBP-reactive $CD4^+$ human T-cells in vitro and are anticipated to be effective by the same mechanism when administered via i.v. route in humans. The same epitopic peptides are anticipated to be effective in inducing suppression of autoimmune attack of human neural tissue when administered to humans orally. The present inventors also have evidence that a whole MBP (which encompasses the foregoing two immunodominant epitope regions) can induce suppression via elicitation of suppressor T-cells (active suppression) when MBP is orally administered in small amounts and in multiple doses. The same antigen, also administered orally but in high amounts and a single dose will induce suppression via anergy. Finally, there is evidence that both mechanisms of suppression can be triggered by adjustment of the oral administration protocol from MBP between the two extremes identified above.

Without wishing to be bound by theory, it is believed that the oral or enteral administration of immunodominant fragments of MBP can cause suppressor T-cells to be elicited that in turn suppress the T-cells that contribute to the autoimmune attack of a neural tissue (i.e., the brain, spinal cord, peripheral nerves or associated cell types). Nerve tissue damage constituting the pathology seen in patients suffering from MS is believed to be the direct result of such an autoimmune attack. As this tolerizing mechanism involves the active induction of regulatory (suppressor) T-cells responsible for the suppression of the immunoreactivity of cells in the vicinity of tissue under immune attack, it is an example of active suppression.

The present inventors have accumulated a large body of experimental evidence that active suppression takes place by the elicitation of tolerizing-antigen specific T-suppressor cells which are targeted to the locus (locuses) of the body where the antigen to which these T-suppressors are specific can be found. This locus includes the tissue under autoimmune attack. Once they encounter this antigen, the T-suppressors secrete suppressive cytokines such as the non-specific immunosuppressive factor TGF-$\beta$, and interleukin-4 (IL-4) which suppress autoimmune responses including autoimmune attack. (See related patent application Ser. No. 843,752.)

In contrast, intravenous administration (or subcutaneous, or intraperitoneal administration) of the MBP fragments incorporating immunodominant epitopes is believed to bring about immune suppression through another mechanism known as clonal anergy. Clonal anergy, or T-cell unresponsiveness, has been attributed to antigen presentation in the absence of the appropriate co-stimulatory factors. Jenkins, M. K. *PNAS.* 84:5409–5413, 1987. The exact identity of the factors involved is illdefined, but soluble cytokines (e.g. B-7, EDCI, and an appropriate intracellular calcium concentration) have been implicated. More recent evidence, however, suggests that so-called "negative signals" rather than the absence of co-stimulatory factors are responsible for anergy. However, these signals have not yet been defined. See, LaSalle J. M. et al, *J. Exp. Med.*, 176:177–186, June 1992. Rather than inducing the T-cell clones to proliferate, presentation of antigen by the APCs without the co-stimulatory factors (and/or in the presence of the negative signals) causes the T-cells to become unresponsive to subsequent antigen stimulation, while remaining responsive to IL-2, and are thus described as being anergized (Jenkins et al., *Proc. Natl. Acad. Sci.* 84:5409, 1987; Mueller et al. *Ann. Rev. Immunol.* 7:455, 1989; Schwartz et al., *Science* 248:1349, 1990). Thus, autoimmune response-promoting clones specific to an autoantigen such as MBP, will no longer proliferate in response to that antigen, reducing the immune attack reactions which cause the tissue damage responsible for the autoimmune disease symptoms, such the neural tissue damage observed in MS.

Suppression by clonal anergy can be differentiated (and has been so differentiated in the experiments below) from active suppression by adoptive transfer experiments which test the ability or inability of suppressor T-cells transferred from a tolerized animal to a nontolerized animal to bring about suppression of immune function in the latter animal. T-cell transfer brings about suppression if the suppression mechanism is active, i.e. if it involves elicitation of T-suppressor cells and does not occur if the suppression mechanism is passive, i.e. if clonal anergy is involved. The results reported in Example 2 illustrate instances in which each mechanism of immune suppression is involved and show that the suppression mechanism depends on one or more of the following: (i) on the substance being administered to induce tolerance (for example, immunodominant epitopic fragments of MBP induce active suppression via the oral route and energy via the parenteral route); (ii) on the route of administration of the tolerizing antigen (for example, only epitopes that are recognized by attack T-cells induce anergy via i.v. route); and (iii) on the amount and frequency of administration (for example, orally administered MBP induces active suppression when given in small amounts and multiple doses and passive suppression when given orally in large amounts and a single dose).

The data show that both encephalitogenic and nonencephalitogenic fragments of MBP can elicit active suppression when orally administered, with those non-encephalitogenic fragments which incorporate an immunosuppressive epitope working only via active suppression and only when administered via the oral route. The encephalitogenic fragments (incorporating an immunodominant epitope) may also elicit anergy via the oral route if administered in high amounts and single doses.

These results have important ramifications on the design of tolerizing agents and methods based on MBP as a tolerizer. Thus, depending on the type of immune suppression desired, particular methods of administration, as well as particular fragments, may be used. For example, it may be desirable to use one or more disease-propagating epitopic peptides via the i.v. or s.c. or i.p. route and (concurrently) one or more immunosuppressive epitopic peptides via the oral route.

It is also anticipated that tolerizing methods involving combinations of administration routes, and/or protocols and/or autoantigen fragments may prove to be most effective. As will be understood by those skilled in the art, the effectiveness of a fragment or combination of fragments (or a combination of a fragment and whole antigen) and the effectiveness of a method (or combination of-methods) of administration of a MBP fragment is a function of the age, sex, weight, physical condition, and disease stage of the subject to be treated, and the concurrent use or absence of other fragments or treatments. Consequently, the fragment (s) used and the method of administration must be determined in substantial part based on these factors, and may need to be determined experimentally on a case by case basis. Such determination, however, requires no more than routine experimentation, given the examples and guidelines contained herein.

Peptides based on the sequences of human MBP for use in the present invention, as identified in Example 1, can be synthesized using well-known solid phase methods (Merrifield, R. B. *Fed. Proc. Soc. Ex. Biol.*, 21: 412, 1962 and *J. Am. Chem. Soc.* 85:2149, 1963; R. Mitchell A. R. et al, *J. Am. Chem. Soc.* 98:7357, 1976; Tam, J. et al., *J. Am. Chem. Soc.* 105:6442, 1983), preferably using a commercially available peptide synthesis apparatus (such as that made by Applied Biosystems, Foster City, Calif.) and following the manufacturers' instructions. Alternatively, such peptides can be synthesized by recombinant DNA techniques as is now well-known in the art (Maniatis et al. , *Molecular Cloning: A Laboratory Manual*, Cold Spring Harbor Laboratories, NY, 1982, see pp. 51–54 and pp. 412–30). For example, these peptides can be obtained as DNA expression products after incorporation of DNA sequences encoding the desired fragment of MBP isolated from the desired species into expression vectors and introduction of such vectors into suitable eukaryotic or prokaryotic hosts that will express the desired peptides individually or as part of fusion peptides or proteins, from which they can be later isolated using well-known techniques.

Peptide analogs can be designed using the known amino acid sequences encoded by the human MBP gene as disclosed below, using the synthetic or recombinant techniques described above and the methods of, e.g., Eyler, E. B., in *Advances in Experimental Medicine and Biology* 21: 259–281, 1978. For example, a peptide having a sequence based upon but differing from the exact amino acid sequence of the desired fragment of MBP can be chemically synthesized using the above-described techniques. Such a peptide can be tested for its effect on MBP-reactive CD4$^+$ T-cells using e.g. the procedure described in Example 1 for identifying a more precise location within amino acids 84–102 for this particular immunodominant epitope of human MBP or the procedure described in Example 4 for testing binding to the T-cell receptor and to the MHC. An MBP-based peptide can be tested in vitro for effectiveness orally in humans by exposing collected, isolated peripheral MBP-specific suppressor T-cells from individuals to the peptide to determine whether they proliferate. Additionally, or alternatively, these isolated suppressor T-cells can be tested to determine whether they release suppressive cytokines such as TGF-β and/or IL-4 upon exposure to an MBP peptide. (See, e.g. the use of the transwell system in co-pending U.S. application Ser. No. 843,752 corresponding to PCT US92/01705 except that the use of spleen cells as APC's is not necessary; the MBP peptide can be used to induce the cells to release TGF-β.) MBP specific T-suppressor cells can be isolated by exposure to MBP and assessment of proliferation followed by binding studies using anti-CD8$^+$ antibody.

The present invention also provides pharmaceutical formulations and dosage forms for oral or parenteral use in the suppression of autoimmune attack T-cell function in humans, particularly those subjects suffering from MS. In general such dosage forms contain one or more peptides according to the invention which are fragments of human MBP and analogs thereof, in an amount effective to suppress proliferation of immune attack cells. Suppression of function which results in an in vitro suppression of immune attack cells, such as MBP-specific CD4$^+$ T-cells and/or attenuation of one or more symptoms of MS in a patient that has been treated pursuant to the method of the present invention is considered to be within the scope of the invention. See definitions section above for what constitutes suppression and symptoms attenuation.

The T-cell suppressive peptides of the present invention may also encompass additional non MBP-derived amino acid sequences leading or following the MBP-based sequences as long as these additional sequences do not defeat the suppressive function of such peptides. Testing of such constructs for immunosuppressive activity can be easily done using, for example, one or more of the assay methods described herein.

The pharmaceutical formulations of the present invention may include, as optional ingredients, pharmaceutically acceptable vehicles, carriers, diluents, solubilizing or emulsifying agents, and salts of the type that are well-known in the art. Nonlimiting examples of such substances include 0.5N saline in distilled water for parenteral use and lactose for oral use.

The fragments of human MBP can be administered orally or by-inhalation in conjunction with synergists which may enhance the effectiveness of the immune suppression. Non-limiting examples of synergists for use in the present invention include bacterial lipopolysaccharides from a wide variety of gram negative bacteria such as various subtypes of *E. coli* and Salmonella (LPS, Sigma Chemical Co., St. Louis, Mo.; Difco, Detroit, Mich.; BIOMOL Res. Labs., Plymouth, Pa.), Lipid A (Sigma Chemical Co., St. Louis, Mo.; ICN Biochemicals, Cleveland, Ohio; Polysciences, Inc., Warrington, Pa.) and immunoregulatory lipoproteins, such as peptides covalently linked to tripalmitoyl-S-glycarylcysteinyl-seryl-serine ($P_3$ C55) which can be obtained as disclosed in Deres, K. et al. (*Nature*, 342:561–564, 1989) or "Braun's" lipoprotein from *E. coli* which can be obtained as disclosed in Braun, V., *Biochim. Biophys. Acta* 435:335–337, 1976. LPS is preferred and Lipid A particularly preferred. Lipid A is particularly preferred for use in the present invention because it is less toxic than the entire LPS molecule. LPS for use in the present invention can be extracted from gram-negative bacteria and purified using the method of Galanes et al. (*Eur. J. Biochem.* 9:245, 1969) and Skelly, R. R., et al. (*Infect. Immun.* 23:287, 1979).

The effective amount of a synergist, e.g. LPS or Lipid A, to be administered in conjunction with the MBP fragment broadly ranges between about 0.15 and 15 mg per kg body weight of said mammal per day and preferably between about 0.3 and 12 mg per kg body weight of said mammal per day.

The route of administration of the suppressive agents of the present invention is in an oral or parenteral form or combinations thereof. Oral administration includes oral, enteral or intragastric administration with oral being preferred. Parenteral administration includes intraperitoneal, subcutaneous, intradermal and most preferably intravenous administration routes.

In general, the MBP-based peptide or analog is administered orally to a human patient in an amount ranging between about 10 μg and about 20 mg per administration. preferably between about 100 μg and 250 μg. The amount is pulse-administered in a single dosage form or multiple dosage forms. For whole MBP to elicit active suppression a dosage of 1 mg five times daily is an example of an effective amount. For anergy, 10–20 mg of MBP parenterally are examples of an effective amount. Monitoring of the patient is desirable in order to optimize the dosage and frequency of administration. The exact amount and frequency of administration to a patient may vary depending on the stage, frequency of manifestation and severity of the patient's disease and the physical condition of the patient, as is well-appreciated in the art. Such optimization is preferably effected on a case-by-case basis. Optimization of the dosage necessary for immune suppression does not represent undue experimentation, given the guidelines disclosed herein.

In an alternative preferred embodiment of the present invention pharmaceutical oral formulations or dosage forms according to the present invention can also be administered by inhalation, preferably in aerosol form. The inhalation mode of administration is preferably not through the nasal passages but through the bronchial and pulmonary mucosa. The MBP fragment and related compounds of the present invention can be administered to humans as dry powder particles or as an atomized aqueous solution suspended in a carrier gas (e.g. air or $N_2$). Preferred aerosol pharmaceutical formulations may comprise for example, a physiologically acceptable buffered saline solution.

The methods of the present invention may involve by-inhalation administration of pharmaceutical formulations in the form of an aerosol spray using for example, a nebulizer such as those described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971 and U.S. Pat. No. 4,635,627 issued Jan. 13, 1971. The aerosol material is inhaled by the subject to be treated.

Other systems of aerosol delivery, such as the pressurized metered dose inhaler (MDI) and the dry powder inhaler as disclosed in Newman, S. P. in *Aerosols and the Lung*, Clarke, S. W. and Davia, D. eds. pp. 197–224, Butterworths, London, England, 1984, can be used when practicing the present invention.

Aerosol delivery systems of the type disclosed herein are available from numerous commercial sources including Fisons Corporation (Bedford, Mass.), Schering Corp. (Kenilworth, N.J.) and American Pharmoseal Co. (Valencia, Calif.).

It is expected that lower amounts of the fragment of MBP of the present invention will be required using aerosol administration for treatment as this effect has been found when treating EAE with whole MBP and adjuvant arthritis with collagen as disclosed in co-pending U.S. patent application Ser. No. 454,486 filed Dec. 20, 1989. Further, it appears that the immune suppression induced by inhalation of the fragment of MBP occurs through the active suppression mechanism, similar to oral administration. Weiner, H. L. et al *FASEB* 4(7):2102, 1990. The amounts of the fragment of MBP of the present invention which may be administered in an aerosol dosage form would be between about 0.015 mg and about 1.5 mg per kg body weight of a mammal per day and may optionally include a synergist in amounts ranging between about 0.05 and about 15 mg per kg body weight of said mammal per day and may be administered in single dosage form or multiple dosage forms. The exact amount to be administered will vary depending on the state and severity of a patient's disease and the physical condition of the patient.

Dosage forms for parenteral administration will generally contain from about 1 to about 200 mg of a peptide according to the present invention per dose per person and preferably about 10 mg to about 100 mg. The foregoing description of inert optional ingredients and fine-tuning of amounts and administration scheduling given above with respect to oral formulations pertain to parenteral formulations only.

It will be appreciated that the unit content of active ingredient or ingredients contained in an individual oral or parenteral dose of each dosage form need not in itself constitute an effective amount for treating MS since the necessary effective amount can be reached by administration of a plurality of dosage units.

The techniques described below in Examples 1–3 can be used to monitor the effectiveness of the methods of the present invention and optimize the amount and frequency of administration of the disease suppressive agents of the present invention, as well as the fragments and method of administration used.

T-cells can be isolated from a patient's peripheral blood or cerebrospinal fluid, amplified and cloned as described in Examples 1–3 (before and/or after treatment according to the present invention). Antibodies (either polyclonal or monoclonal) can be obtained directed against the MBP peptides of the present invention (using conventional techniques well known and used in the art) to assay for the presence of MBP-reactive T-cells in a patient's peripheral blood and more specifically for the presence of activated MBP-reactive CD4+ T-cells before and/or after treatment according to the present invention. The peptides of the present invention are also useful in identifying individuals with T-cells reactive with MBP, using the method of Example 1.

The present invention is described further below in specific working examples which are intended to illustrate the present invention without limiting its scope.

EXAMPLE 1

IDENTIFICATION OF THE MAJOR IMMUNODOMINANT REGION OF HUMAN MBP

MBP was extracted from human brain tissue and purified on a CM-52 column (Supplier: Wattman Biosystems Ltd Maidstone, Kent, U.K.) using the highest molecular weight peak (18 kD) as described (Chou, F. C.-H. et al., *J. Biol. Chem.* 251:2671, 1976). MBP peptides were synthesized using a solid phase method or were obtained from a commercial laboratory (Biosearch Lab Inc., San Raphael, Calif.) and were purified by high pressure liquid chromatography as follows: Each peptide containing preparation was made up in 0.1% trifluoroacetic acid (TFA) at 1 mg/ml. It was then processed in an HPLC column (Rainin Reverse Phase C4 or C18) using a 0–70% acetonitrile gradient containing 0.1% TFA. Peaks were detected at 214 nm. The MBP peptide fragments used are set forth below in Table 1. However, the sequence of human MBP is published. Therefore, only the numbers designating the amino acid residues contained in each peptide are necessary.

TABLE 1

| Human MBP Amino Acid Residues | Sequence | Human MBP Amino Acid Residues | Sequence |
| --- | --- | --- | --- |
| 1–20: | ASQKRPSQRHGSKYLATAST | 11–30: | GSKYLATASTMDHARHGFLP |
| 21–40: | MDHARBGFLPRHRDTGILDS | 31–50: | RHRDTGILDSIGRFFGGDRG |
| 41–60: | IGRFFGGDRGAPKRGSGKDS | 51–70: | APKRGSGKDSHEPARTABYG |
| 61–82: | HHPARTAHYGSLPQKSEGRT | 71–92: | SLPQKSEGRTQDENPVVHFF |
| 84–102: | DENPVVHFFKNIVTPRTPP | 93–112: | KNIVTPRTPPPSQGKGRGLS |
| 113–132: | LSRFSWGAEGQRPGFGYGGR | 124–142: | RPGFGYGGRASDYKSAHKG |
| 143–168: | FKGVDAQGTLSKIFKLGGRD | | |

A rapid T-cell cloning technique was used to examine whether there were immunodominant epitopes on human MBP reactive with Class II MHC phenotypes and the frequency of such reactivity. A total of 15,824 short term T-cell lines were generated from 51 human subjects by culturing peripheral blood mononuclear cells (PMN) with purified MBP (100 µg) followed 3 days later, and then every 3–4 days, by the addition of interleukin-2 (IL-2; from ABI, Columbia, Md.) and 2 units recombinant interleukin-4 (IL-4; Genzyme, Boston, Mass.). On Day 13 of culture, an aliquot from each line was tested for reactivity to MBP using the following proliferation assay: T-cell clones ($1\times10^5$ cells/well) were plated in triplicate and cocultured with appropriate stimuli (i.e. 100 µg whole MBP or 5% IL-2) for 72 hours at 37° C., 90% humidity, 5% $CO_2$, in 96 well flat bottomed microtiter plates (Costar). The cells were pulsed with 2 µCi [$^3$H]TdR (2 Ci/mmole, New England Nuclear, Boston, Mass.) for the last 18 hours of culture. APCs were prepared by pulsing human Epstein-Barr virus transformed human B-cells (the virus being commercially available from ATCC) or L-cells which are mouse cells transfected with human $DR_2$ (L-cells are commercially available from ATCC under accession No. ATCC-CCL1 and can be transfected according to the method of Wilkinson, D. et al, *J. Exp. Med.*, 1988, 167:1442–1458 using DNA encoding DR2 as per Wu, S. et al *J. Immunol.*, 1987, 138:2953). B-cells or L-cells were used at $1\times10^6$ cells/well in complete media either in the presence or absence of 40 pM MBP or phospholipid protein (PLP) for 2 hours at 37° C., washing twice with 4° C. Hanks (Whittaker), followed by irradiation with 5000 rad. at 4° C. To stimulate T-cells without accessory APCs, 2 µM of MBP, PLP, or the appropriate fragment was added directly to the cells for the duration of the culture: 48 hours, followed by pulsing thymogen and then harvesting. Ten thousand APC's were used for 100,000 T-cell clones.

T-cell lines shown to be reactive to MBP or PLP were then tested using the same technique for reactivity to overlapping oligopeptide 20-mers encompassing the human MBP sequence as shown in Table 1 above. MBP and PLP reactivity frequency analysis was performed on patients with definite, relapsing-remitting MS (as diagnosed by Magnetic Resonance Imaging (MRI) and clinical examination), as well as on subjects with other neurologic diseases and on normal subjects (all age- and sex-matched to the MS patients). The results are shown in Table 2 below.

The frequency of MBP-peptide specific cell lines from normal subjects and other neurologic disease controls were virtually identical and thus combined for analysis. The mean frequency of T-cell lines from subjects with MS that were selectively reactive to MBP residues 84–102 was higher as compared with controls (FIG. 1). Significant but less striking increases in reactivity to MBP residues 61–82 and 124–142 were also observed in MS patients, while both MS and

TABLE 2

|  | AGE | SEX (%) (M/F) | #Ag REACTIVE LINES TOTAL # LINES | | MEAN FREQUENCY OF Ag REACTIVE LINES | |
| --- | --- | --- | --- | --- | --- | --- |
|  |  |  | MBP | PLP | MBP | PLP |
| MS* (n = 23) | 34.2 ± 1.4 | 35/65 | 554/7746 | 20/432 | 7.18 ± 2.38 | 3.34 ± 1.56 |
| OTHER N* DISEASE (n=10) | 38.7 ± 3.2 | 43/57 | 118/2880 | 3/384 | 4.10 ± 1.04 | 0.90 ± 0.62 |
| NORMAL (n = 6) | 30.3 ± 1.5 | 50/50 | 73/1742 | ND | 4.70 ± 1.58 | ND |

*MS = Multiple Sclerosis
**N = Neurological

Patients with MS were caucasian and had well-characterized relapsing remitting disease with at least two exacerbations within the previous 24 months and positive lesions as seen using MRI at the time of blood drawing. Subjects with other central nervous system diseases had the following diagnoses: 1–3 weeks after either cerebrovascular accident (n=4), brain trauma with CNS hemorrhage (n=4), or metastatic brain tumor (n=2). The total number of T-cell lines reactive with MBP or PLP and the total number of T-cell lines generated are shown in Table 2 ("Ag" means "antigen"). In addition, the frequency of MBP and PLP-reactive lines was calculated separately for each subject by dividing the number of MBP-reactive lines by the total number of lines generated and the mean values +/–SEM are given. The same conclusions can be drawn regarding reactivity to PLP although to a lesser extent than reactivity to MBP or its fragments.

While the frequency of lines reactive to all fragments of MBP was slightly higher in subjects with MS as compared to the other subjects, this increase was not statistically significant. However, as discussed below, a significantly greater number of the MBP reactive cells lines from MS patients were reactive with the fragments including amino acids 84–102 and 143–168, respectively, thus identifying these peptides and the corresponding fragments of MBP as containing immunodominant epitopes of MBP active in the development of MS.

Of a total of 302 cell lines from patients with MS that could be expanded and confirmed to react with MBP on repeated analysis, 140 (46.4%) reacted with MBP residues 84–102; and approximately 70–80% reacted with either MBP residues 84–102 or 143–168. In the control groups, 11 of a total of 100 MBP reactive T-cell lines (11.0%) recognized the 84–102 peptide and about 34% recognized either the 84–102 or the 143–168 peptide. The actual frequency of T-cells derived from the peripheral blood that reacted with each MBP peptide for each individual subject was calculated. The mean values for patients with MS and the control subjects are shown in the rightmost column of Table 2. The corresponding immunodominant peptide(s) of PLP can be identified by the same methods as described herein for the MBP peptides.

control subjects showed high frequencies of T-cell lines reactive with MBP residues 143–168. IL-2 was used to select the T-cell lines that were activated. After primary stimulation with IL-2 the thus activated cell lines recognized MBP peptides.

Expansion of these findings into a larger population of MS patients was done, using the techniques described above. An additional 132 T-cell lines (63 from MS patients and 88 from normal controls) were studied, with the results reported in Table 3, below. In summary, these results support the conclusion of peptides containing MBP amino acid residues 84–102 and 143–168 as the immunodominant domains of MBP.

TABLE 3

| Subject | Stimulus | No. of MBP-Peptide Reactive Lines | Peptide Reactivity (Fraction of MBP-Reactive Lines) |
| --- | --- | --- | --- |
| MS-HY | MBP | 17 | 84–102 (17/17) |
|  | IL-2 | 4 | 84–102 (4/4) |
| MS-SW | MBP | 8 | 84–102 (2/8) |
|  |  |  | 143–158 (5/8) |
|  |  |  | other (1/8) |
|  | IL-2 | 3 | 143–168 (2/3) |
|  |  |  | other (1/3) |
| MS-CY | MBP | 14 | 143–168 (9/14) |
|  |  |  | other (5/14) |
|  | IL-2 | 4 | 143–168 (3/4) |
|  |  |  | other (1/4) |
| MS-HK | MBP | 7 | 143–168 (6/7) |
|  |  |  | other (1/7) |
|  | IL-2 | 6 | 143–168 (5/6) |
|  |  |  | other (1/6) |
| MS-JA | MBP | 10 | 84–102 (1/10) |
|  |  |  | 143–168 (8/10) |
|  | IL-2 | 4 | 143–168 (4/4) |
| MS-MI | MBP | 5 | 84–102 (3/5) |
|  |  |  | 143–168 (1/5) |
|  |  |  | other (1/5) |
|  | IL-2 | 2 | 84–102 (1/2) |
|  |  |  | 143–168 (1/2) |
| MS-AN | MBP | 2 | 143–168 (2/2) |
|  | IL-2 | 2 | 143–168 (2/2) |
| MS-ST | MBP | nd | nd |

TABLE 3-continued

| Subject | Stimulus | No. of MBP-Peptide Reactive Lines | Peptide Reactivity (Fraction of MBP-Reactive Lines) |
|---|---|---|---|
| | IL-2 | 18 | 84–102 (6/18) |
| | | | 143–168 (6/18) |
| | | | 93–142 (3/18) |
| | | | other (3/18) |
| NS-kw | MBP | 8 | 84–102 (2/8) |
| | | | 143–168 (5/8) |
| | | | other (1/8) |
| | IL-2 | 1 | 84–102 (100%) |
| NS-jl | MBP | 12 | 84–102 (10/12) |
| | | | other (2/12) |
| | IL-2 | 12 | 84–102 (7/12) |
| | | | 143–168 (5/12) |
| NS-aa | MBP | 2 | 84–102 (2/2) |
| | IL-2 | 2 | 84–102 (2/2) |
| NS-dd | MBP | 12 | 84–102 (4/12) |
| | | | 143–168 (6/12) |
| | | | other (2/12) |
| | IL-2 | 2 | 84–102 (1/2) |
| | | | 143–168 (1/2) |
| NS-nb | MBP | 37 | 84–102 (37/37) |
| | IL-2 | 2 | 84–102 (2/2) | nd nd = not not donedone

The foregoing results in Table 4 demonstrate that a dramatically higher number of additional MBP-reactive T-cell clones can be identified in MS patients (compared to controls) upon primary stimulation of MBP-specific T-cells with IL-2. This indicates that MBP-reactive T-cell clones can be de-activated (possibly deanergized) by exposure to IL-2, subsequent to which they become reactive to MBP peptides.

EXAMPLE 2

MECHANISM OF INDUCTION OF IMMUNE TOLERANCE

The experiments in this Example were done to compare the effectiveness of suppression of EAE using different fragments of MBP, to compare oral and intravenous administration of the protein fragment, and to compare treatment of the disease state when it was induced or adoptively-transferred. Induced EAE occurs when MBP is used to immunize a host and is administered intramuscularly in conjunction with an adjuvant, while adoptively transferred disease occurs when an MBP-reactive cell line is activated then injected into the animal. (see *Induction of EAE* section below for details.) In this example, the following materials and methods were used.

Animals. Female Lewis rats 6–8 weeks of age were obtained from Harlan-Sprague Dawley Inc. (Indianapolis,

TABLE 4

| subject | CSF cells/nm$^3$ | frequency of IL-2 responsive T-cells × 10$^{-4}$ CSF | frequency of IL-2 responsive T-cells × 10$^{-4}$ PBMC | CSF | PBMC |
|---|---|---|---|---|---|
| patients with MS | (A) | (B) | (C) | (D) | |
| MS-1 | 12.2 | 18.0 (13.1–25.7)[a] | 4.7 (2.3–8.2) | 2.6 (1.8–6.6) | N.D.[b] |
| MS-2 | 1.5 | 10.4 (6.1–14.7) | 6.7 (4.2–11.8) | 5.5 (4.3–9.2) | N.D. |
| MS-3 | 1.2 | 7.7 (4.3–12.8) | 4.7 (2.9–8.8) | 3.8 (2.2–7.2) | N.D. |
| MS-4 | 1.2 | 16.6 (11.5–23.7) | 13.3 (9.9–19.7) | 9.1 (6.9–14.8) | N.D. |
| MS-5 | 1.5 | 17.5 (13.1–24.2) | 11.2 (7.8–17.2) | 8.3 (5.3–14.5) | N.D. |
| MS-6 | 2.0 | 23.3 (16.9–32.4) | 8.7 (6.4–13.2) | 20.0 (14.8–28.0) | N.D. |
| MS-7 | 3.4 | 25.0 (18.7–33.1) | 7.7 (4.2–12.4) | 8.4 (6.0–13.5) | 1.8 (1.4–3.2) |
| MS-8 | 2.8 | 7.7 (4.3–11.9) | 2.3 (1.7–5.8) | 6.7 (4.2–11.8) | 1.9 (1.3–4.4) |
| MS-9 | 5.0 | 12.1 (8.6–17.8) | 12.1 (8.8–17.4) | 1.7 (1.2–4.3) | N.D. |
| MS-10 | 4.8 | 24.3 (17.2–32.2) | 2.4 (6.4–13.5) | 3.4 (2.3–7.4) | N.D. |
| MS-11 | 5.7 | 23.8 (16.8–32.5) | 3.2 (2.2–7.8) | 4.9 (2.9–8.6) | N.D. |
| MS-12 | 4.6 | 6.1 (3.6–11.1) | 2.7 (1.8–5.6) | N.D. | N.D. |
| MS-13 | 2.2 | 17.8 (13.2–24.3) | 10.0 (7.8–15.4) | N.D. | N.D. |
| MS-14 | 3.4 | 25.0 (18.7–33.5) | 16.6 (11.5–23.5) | 2.4 (1.7–6.9) | N.D. |
| MS-15 | 3.8 | 18.2 (13.4–24.8) | 8.3 (5.8–11.4) | 6.6 (5.2–10.8) | N.D. |
| MS-16 | 4.5 | 6.2 (4.3–11.8) | 4.2 (2.4–7.5) | 6.4 (5.2–10.7) | N.D. |
| MS-17 | 2.6 | 12.5 (8.6–18.3) | 6.2 (4.6–10.8) | 1.4 (1.3–4.5) | N.D. |
| MS-18 | 1.2 | 7.7 (4.2–13.1) | 4.3 (2.7–9.2) | N.D. | N.D. |
| MS-19 | 4.6 | 11.1 (7.6–17.0) | 2.0 (1.4–5.6) | 16.5 (11.5–24.1) | 2.7 (1.8–5.2) |
| MS-20 | 3.8 | 23.8 (16.9–32.0) | 8.3 (6.0–12.9) | N.D. | N.D. |
| mean | 3.60 | 15.7 | 7.8 | 5.4 | 0.32 |
| patients with OND | | (E) | (F) | (G) | (H) |
| OND-1 | 5.0 | 10.4 (7.3–16.4) | 9.6 (7.3–14.6) | N.D. | N.D. |
| OND-2 | 2.0 | 7.2 (5.1–10.8) | 8.3 (5.8–12.4) | N.D. | N.D. |
| OND-3 | 2.4 | 4.6 (2.8–9.0) | 7.8 (4.2–14.5) | N.D. | N.D. |
| OND-4 | 3.0 | 5.8 (4.6–10.1) | 5.4 (4.2–9.9) | N.D. | N.D. |
| OND-5 | 5.0 | 4.1 (2.3–8.5) | 8.7 (6.4–13.4) | N.D. | N.D. |
| OND-6 | 4.4 | 4.8 (2.9–9.2) | 6.8 (5.2–10.2) | N.D. | N.D. |
| OND-7 | 1.2 | 3.3 (2.0–7.9) | 4.2 (2.4–8.9) | N.D. | N.D. |
| OND-8 | 2.0 | 2.1 (1.3–5.0) | 4.9 (3.8–9.1) | N.D. | N.D. |
| mean | 3.13 | 5.2 | 6.9 | | |
| column pair | (A)–(B) | (C)–(D) | (E)–(F) | (A)–(B) | (B)–(F) | (C)–(G) |
| p value[c] | 0.0001 | 0.0001 | 0.165 | 0.001 | 0.578 | 0.0001 |

[a]95% confidence limits.
[b]not detectable at the cell concentration used.
[c]calculated by t-test.

Ind.). Animals were housed in Harvard Medical School Animal Care Facilities and maintained on standard laboratory chow and water ad libitum. Animals were maintained in accordance with the guidelines for the Committee on Care of Laboratory Animals of the Laboratory Research Council (Pub. #DHEW:NIH, 85–23, revised 1985).

Antigens and Reagents. Guinea pig MBP was purified from brain tissue by the modified method of Deibler et al. (Prep. Biochem. 2:139, 1972). Protein content and purity were checked by gel electrophoresis and amino acid analysis. Concanavalin A and histone were obtained from Sigma (St. Louis, Mo.). Peptides were synthesized in the peptide facility of the Center for Neurologic Disease, Brigham and Women's Hospital, and purified on HPLC. The amino acid sequences of the peptides synthesized are: 21–40, MDHAR-HGFLPRHRDTGILDS (immunosuppressive epitope region when orally administered to rats); 71–90, SLPQKSQR-SQDENPVVHF (immunodominant encephalitogenic region in rats); 151–170, GTLSKIFKLGGRDSRS.

Induction of Tolerance. For oral tolerance or active suppression, rats were fed 1 mg of MBP dissolved in 1 ml PBS, or PBS alone, by gastric intubation with a 18-gauge stainless steel animal feeding needle (Thomas Scientific, Swedesboro, N.J.). Animals were fed five times at intervals of 2–3 days with the last feeding two days before immunization. For intravenous tolerance or clonal anergy, rats were injected with 0.1 mg of MBP, MBP peptides, or histone dissolved in 0.1 ml PBS, or PBS alone. Animals were injected via the ocular vein five times at intervals of 2–3 days with the last injection two days before immunization.

Induction of EAE. For actively induced disease, Lewis rats were immunized in the left foot pad with 25 $\mu$g of guinea pig MBP in 50 $\mu$l of PBS emulsified in an equal volume of complete Freund's adjuvant (CFA) containing 4 mg/ml of mycobacterium tuberculosis (Difco). For adoptively transferred EAE, an MBP active T cell line was established from rats immunized with MBP in CFA, raised and maintained according to the method of Ben-Nun et al. (Euro. J. Immunol. 11:195, 1982). Encephalitogenic cells were collected after activation by culture with Concanavalin A (ConA) (2 $\mu$m/ml) using irradiated thymocytes from immunized animals as APCs. Cells were harvested from cultures via a ficol hypaque gradient (Hypaque 1077, Sigma) and washed twice in PBS prior to transfer. $5 \times 10^6$ encephalitogenic cells were injected intraperitoneally in 0.1 ml PBS into irradiated (750 rads, 24 hrs. earlier), recipient rats. Cell viability of both modulator and encephalitogenic cells was determined by trypan blue exclusion and was greater than 90%. In all experiments 5 animals were used per experimental group.

Purification of T cell subsets for adoptive transfer of protection following oral tolerization. Depletion of lymphocyte subsets was performed by negative selection using magnetic beads according to a modified method of Cruikshank et al. (J. Immunol. 138:3817, 1987). Spleen cells were incubated with a 1:10 dilution of mouse anti-rat CD8 or CD4 monoclonal antibody (clones OX/8 or W3/25 respectively, Serotec/Bioproducts, Indianapolis, IN), for 30 minutes on ice, washed twice, and then added to prewashed magnetic particles, with an average diameter of 4.5 $\mu$m (M-450) with goat anti-mouse IgG covalently attached (Dynal, Fort Lee, N.J.). The quantity of magnetic beads used was calculated as being 10 times the estimated target cell population. The cells were incubated with the beads in 0.5 ml of RPMI 1640 medium supplemented with 10% fetal calf serum in a 10 ml round bottom test tube (Nunc) for 30 min. on ice with gentle shaking every 5 min. After incubation, the bead/cell suspension was washed with 5 ml of medium, and the cell-mAb-bead complexes were separated from unlabeled cells in a strong magnetic field using a magnetic-particle concentrator (Dynal-MPC-1) for 2 minutes. The supernatant was removed, and the procedure was repeated twice to obtain the nonadherent fraction. The cells in the $CD4^+$ and $CD8^+$ depleted populations were $>95\% CD4^+CD8^-$ or $CD4^-CD8^+$, as demonstrated by indirect flow cytometry. Whole spleen populations from MBP fed or control animals were cultured ($5 \times 10^6$ cells in 1 ml of proliferation media), in the presence of Con-A (2 $\mu$g/ml). Depleted populations were cultured at a concentration of $2.5 \times 10^6$ cells per ml. The resulting subsets were used as modulator cells.

Clinical evaluation. Animals were evaluated in a blinded fashion every day for evidence of EAE. Clinical severity of EAE was scored as follows: 0, no disease; 1 limp tail; 2, hind limb paralysis; 3, hind limb paraplegia, incontinence; 4, tetraplegia; and 5 death. Duration of disease was measured by counting the total number of days from disease onset (usually days 10 or 11 after active immunization and 3–5 days after adoptive transfer of disease) until complete recovery for each animal.

Delayed type hypersensitivity (DTH) testing. DTH was tested by injecting 25 $\mu$g of MBP in PBS subcutaneously in the ear. Thickness was measured by a blinded observer, before and 48 hours after challenge, using micrometer calipers (Mitutoyo, Japan). The difference of ear thickness before and after challenge was recorded for each animal, and the result was expressed as the mean for each experimental group±SEM.

Histology. Histologic analysis of pathological changes was performed in rats with adoptively transferred EAE. Spinal cords were removed on day 15 after adoptive transfer and fixed with 10% neutral buffered formalin. Paraffin sections were prepared and stained with Luxol fast blue-hematoxylin and eosin, by standard procedures (Sobel et al., J. Immunol. 132:2393, 1984). Spinal cord tissue was sampled in an identical manner for each animal and numbers of inflammatory foci per section (clusters of >20 or more aggregated inflammatory cells), in parenchyma and meninges were scored in a blinded fashion (Sobel et al., supra).

Statistical analysis. Clinical scales were analyzed with a two-tailed Wilcoxon rank sum test for score samples, chi square analysis was used in comparing the incidence of disease between groups, and comparison of means was performed by using the Student's t-test. For individual experiments, 5 animals were used per group.

RESULTS

Suppression of adoptively transferred RAE by oral tolerization to MBP. To evaluate the effect of prior oral administration of MBP on adoptively transferred EAE, MBP-fed and control rats were intraperitoneally inoculated with $5 \times 10^6$ MBP-specific, Con-A stimulated, encephalitogenic line cells. MBP reactive cells were transferred 2 days after the last feeding. FIG. 2A graphs the clinical scores of animals which were orally tolerized to MBP and then inoculated with the MBP-specific cells (black circles) and compares them with the clinical scores of naive animals similarly inoculated (open circles). As shown in this figure, oral administration of MBP had no effect on adoptively transferred EAE. The present inventors propose that the failure of oral tolerization to suppress adoptively transferred EAE is due to the fact that the transplanted encephalitogenic T-cells are activated and able to migrate to the target organ rapidly wherein they initiate immune attack before sufficient numbers of suppressor T-cells: migrate to the lymph nodes; and (iii) migrate to the target organ (brain). Thus, the ratio of regulatory to encephalitogenic cells present at the target organ and the timing of their entry appear to be critical.

However, adoptively transferred EAE was suppressed when spleen cells from orally tolerized animals were co-transferred with the encephalitogenic cells to naive recipients (FIG. 2B), indicating that already-elicited suppressor T-cells can successfully prevent disease even when they are co-administered with the immune attack cells.

FIG. 2B graphs the clinical scores of animals which were co-injected with $5 \times 10^6$ encephalitogenic cells with $1.5 \times 10^6$ spleen cells from animals orally tolerized to MBP. For co-transfer, cells from orally tolerized animals were mixed with encephalitogenic cells and injected (black circles). As also shown in FIG. 2B, similar protection was observed when encephalitogenic and modulator cells were injected separately in the right and left flanks (open circles), which indicates that the protective effect is not due to interaction between suppressor T-cells and attack T-cells. The clinical scores of positive control animals in FIG. 2B are indicated by black squares.

Figure 3:
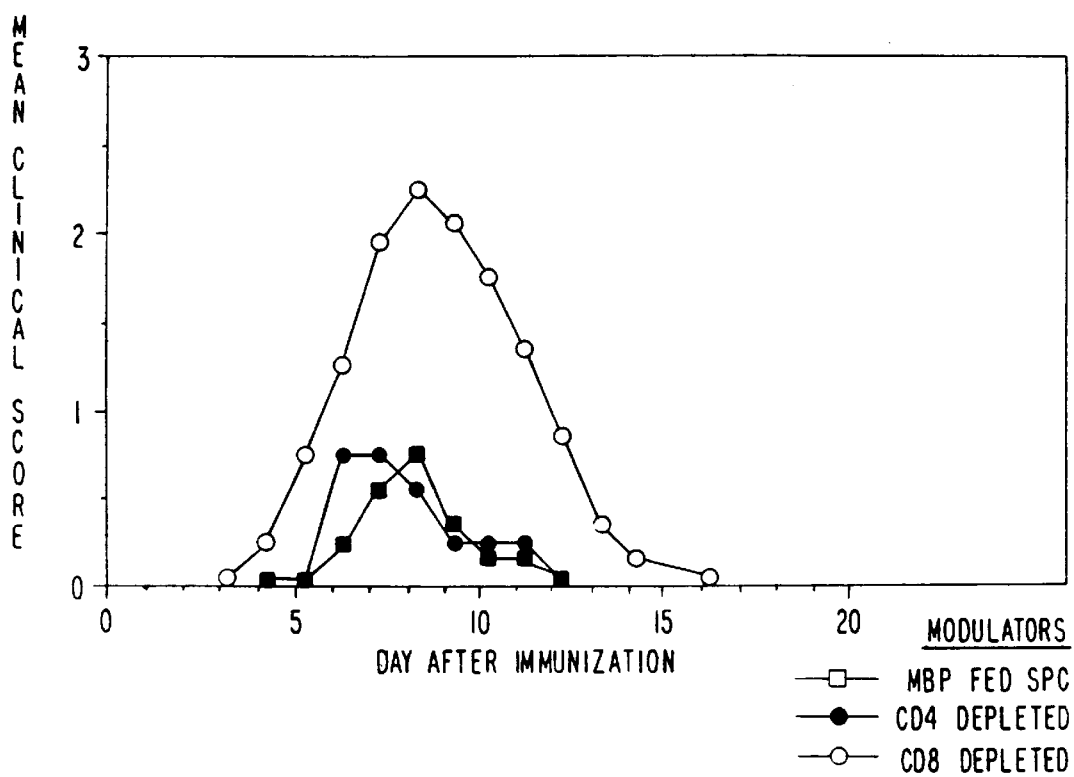
FIG. 3 depicts the suppression of adoptively transferred EAE by co-transfer of CD4$^+$-depleted or CD8$^+$-depleted T-cells from MBP fed animals.

Suppression of adoptively transferred EAE is dependent on $CD8^+$ T cells from orally tolerized animals. To determine whether suppression of adoptively transferred EAE was dependent on a specific T-cell subset, spleen cells from MBP fed animals were depleted on $CD4^+$ or $CD8^+$ T-cell subsets prior to adoptive transfer and used as modulators. As shown in FIG. 3, adoptive transfer of protection was abrogated by transfer of $CD8^+$ depleted spleen cells, but not by transfer of $CD4^+$ depleted spleen cells (mean maximal score=2.3±0.2 vs. 0.7±0.2, respectively, p<0.01). Open squares: unselected spleen cell population, black circles $CD4^+$ depleted spleen cells; open circles $CD8^+$ depleted spleen cells.

Figure 4:
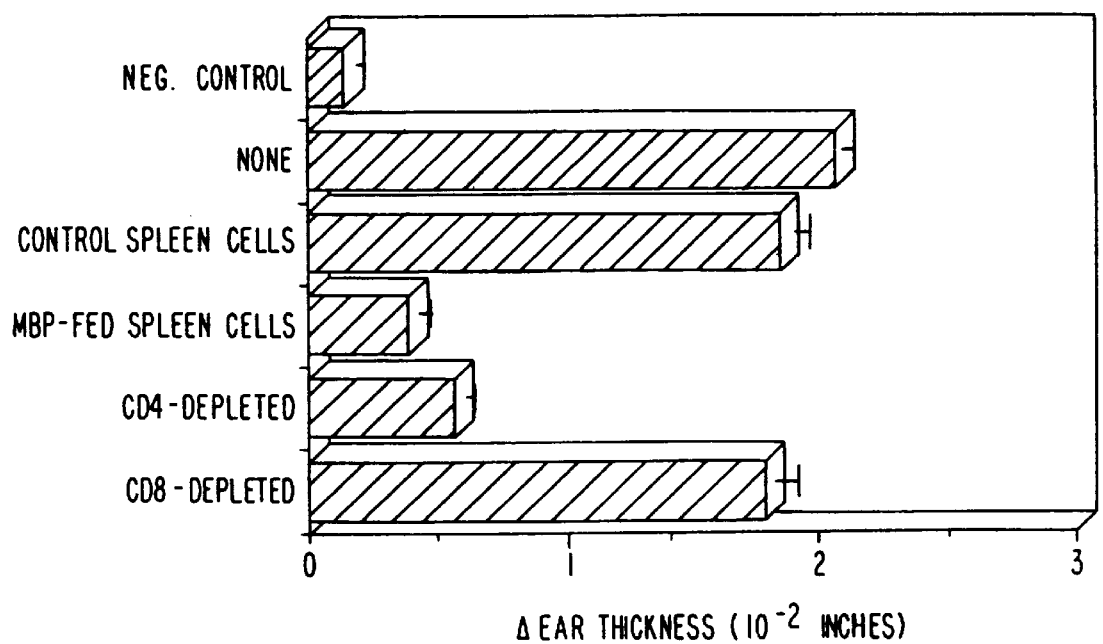
FIG. 4 is a bar graph of DTH responses associated with the extent of protection (if any) against EAE induction by co-transfer along with CD4$^+$ T-cells of various T-cell subsets from MBP fed animals.

Delayed type hypersensitivity (DTH) responses associated with adoptively transferred EAE. A correlation between DTH responses and the suppression of actively induced EAE following oral tolerance has been found (Miller et al., J. Exp. Med. 174:791, 1991; Miller et al., Proc. Natl. Acad. Sci. 89:421, 1992). To determine whether a similar correlation existed in adoptively transferred EAE, DTH responses were measured. As shown in FIG. 4, prominent DTH responses developed in animals undergoing adoptively transferred EAE and DTH responses were suppressed by the co-transfer of splenocytes from animals orally tolerized to MBP. The suppressed DTH responses were abrogated by depletion of $CD8^+$, but not $CD4^+$ T-cells prior to transfer. (Δ ear swelling $CD4^+$ depleted vs. $CD8^+$ depleted=0.6±0.1 vs. 1.8±0.2, p<0.01).

Figure 5:
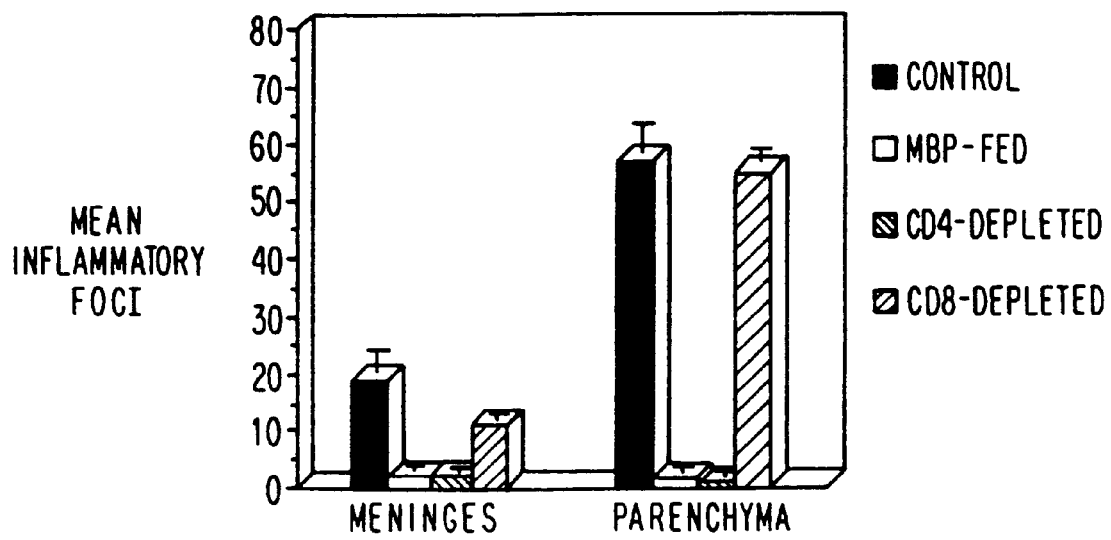
FIG. 5E is a bar graph of quantitative histologic analysis expressed in mean number of inflammatory foci isolated from the CNS (i.e., the parenchyma and the meninges) of mice injected with various T-cell subsets from MBP-fed mice.
FIGS. 5A–5D are histographs of CNS of mice injected with the foregoing T-cell subsets (5A: control; 5B: CD4+ depleted; 5C: CD$_8$+depleted; and 5D: MBP fed).

Effect of co-transfer of cells from MBP orally tolerized animals on CNS histology in adoptively transferred EAE. Oral administration of MBP suppresses CNS inflammation in actively induced EAE (Higgins et al., J. Immunol. 140:440, 1988). Nevertheless, not all immune specific immunomodulatory treatments of EAE that suppress clinical disease affect CNS inflammation (Offner et al., Science 251:430, 1991). As shown in FIG. 5, there was decreased inflammation in both the parenchyma and meninges when cells from MBP-fed animals were transferred and this suppression was observed when $CD4^+$ depleted, but not $CD8^+$ depleted modulator spleen cells from orally tolerized animals were transferred. Number of CNS (parenchyma+ meninges) inflammatory foci for the specific groups were as follows: Control=76±8.2; MBP fed=3.8±1.8; $CD4^+$ depleted=2.8±1.0; $CD8^+$ depleted=65±4; (p<0.01, MBP fed and $CD4^+$ depleted vs. control or $CD8^+$ depleted).

Figure 6A:
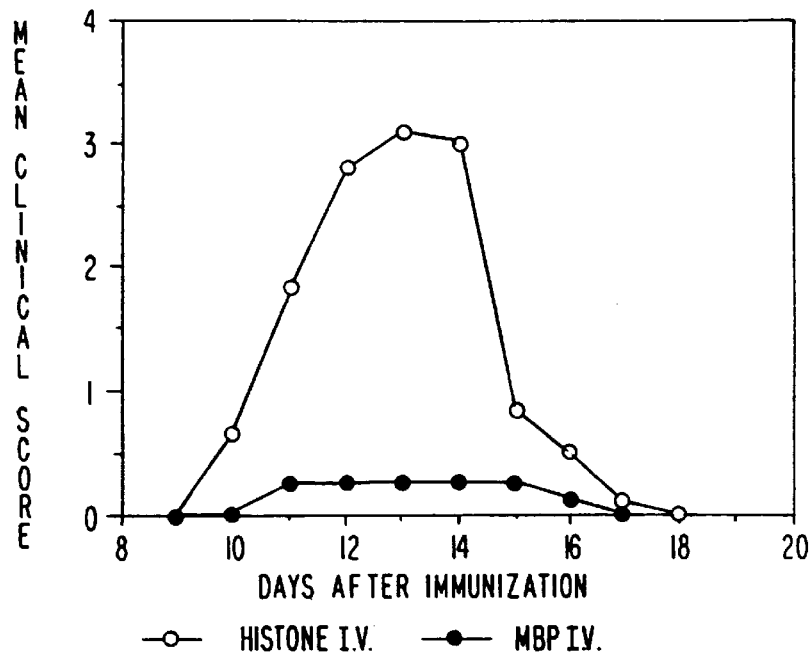
FIG. 6, in graph A, depicts the suppression of actively induced EAE by intravenous (IV) administration of MBP.
Figure 6B:
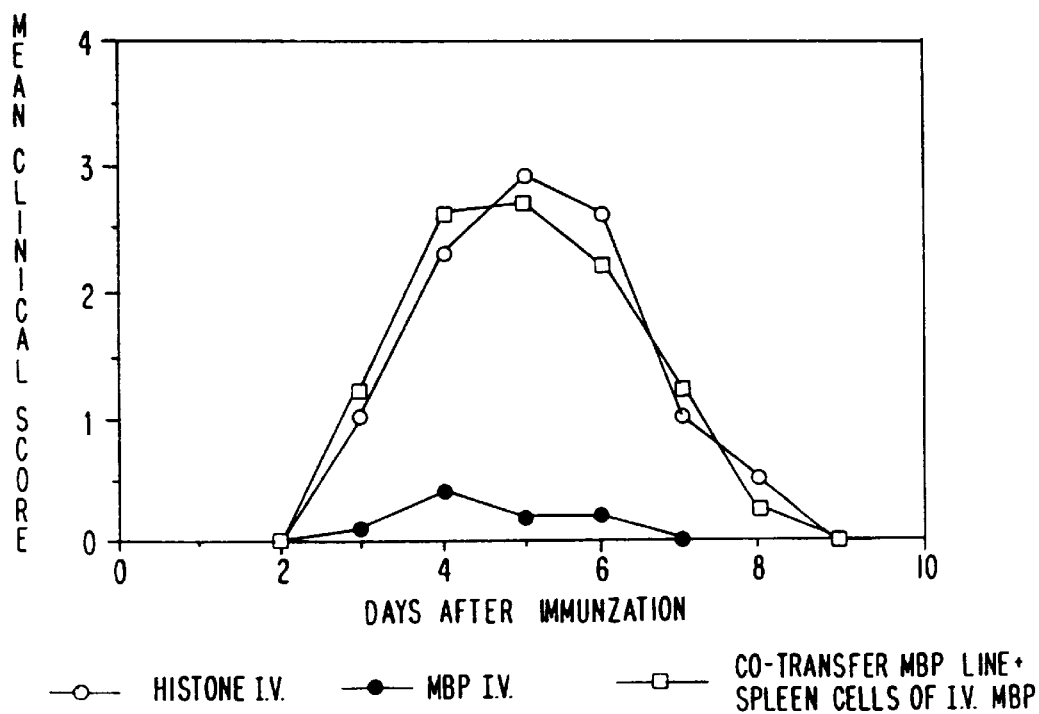

Suppression of actively induced and adoptively transferred EAE following IV administration of MBP. As shown in FIG. 6A, intravenous (IV) injection of MBP markedly suppressed EAE actively induced by immunization with MBP/CFA (mean maximal score =0.5±0.2, vs. control injected histone=3.0±0.3; p<0.01), in an analogous manner to suppression by oral tolerization with MBP. In contrast to oral tolerization, however, which did not protect against adoptively transferred EAE (FIG. 2A), IV injection of MBP also suppressed adoptively transferred EAE (mean maximal score=0.4±0.2, vs. control=3.2±0.2; p<0.01). (FIG. 6B) However, unlike oral tolerization, disease protection could not be adoptively transferred with spleen cells from IV tolerized animals when such cells were co-transferred with an MBP encephalitogenic line (mean maximal score= 2.8±0.2, vs. control p=N.S. (FIG. 6B).

Figure 7A:
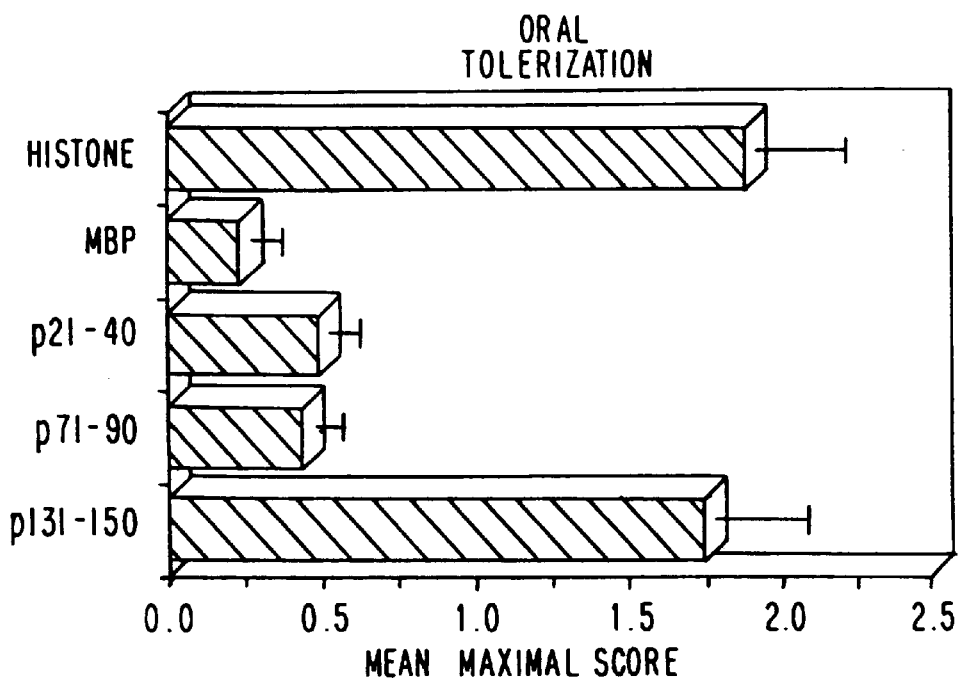
FIG. 7 is a bar graph showing the variation in suppression of EAE following oral (7A) or IV (7B) administration of different MBP peptides.
Figure 7B:
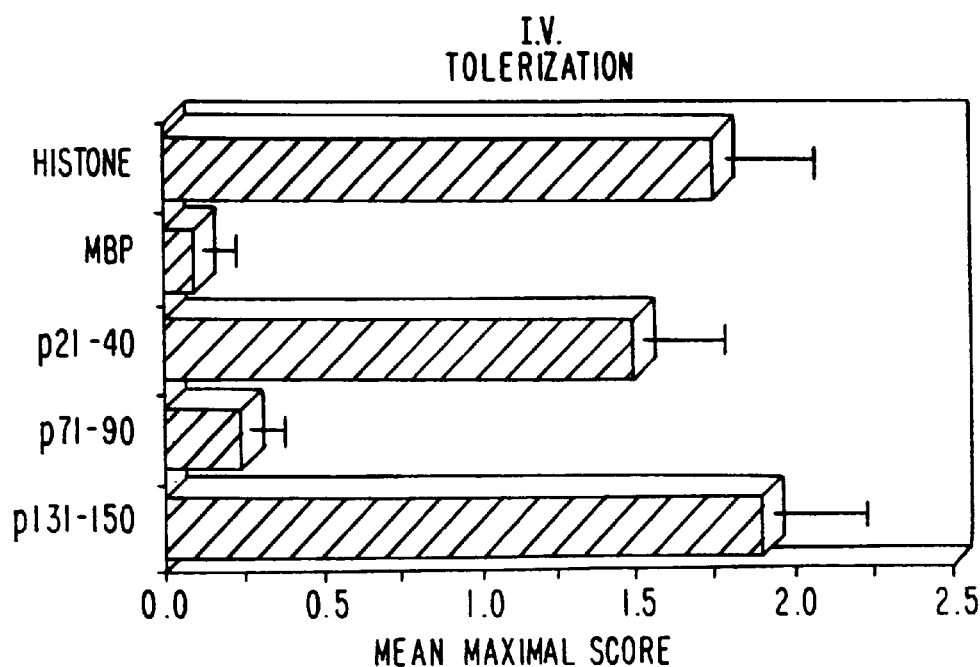

Suppression of EAE following oral or IV administration of MBP Reptides. To further investigate the mechanism of oral vs. IV tolerance, MBP peptides encompassing both encephalitogenic and non-encephalitogenic regions of MBP were administered both orally and intravenously prior to immunization for actively induced disease. MBP peptide 71–90 of guinea pig MBP is encephalitogenic in Lewis rats (Swanborg et al., J. Immunol. 114:191, 1975). As shown in FIG. 7, suppression of EAE via IV tolerization only occurred with whole MBP and encephalitogenic peptide 71–90, but not with guinea pig MBP peptide 21–40. Oral tolerization with 21–40, however, was effective in suppressing EAE. Guinea-pig peptide 21–40 was chosen as experiments demonstrated that it triggered TGF-β release from spleen cells of rats orally tolerized to whole MBP. Miller, A. et al. FASEB 6:1686, 1992. Control guinea pig MBP peptide 131–150 did not suppress when administered either orally or intravenously. Of note is that in addition to suppressing via the IV route, encephalitogenic MBP peptide 71–90 also suppressed when given orally. This result indicates that peptides derived from the immunodominant domain of a given MBP towards a given host can suppress T-cell function when they are orally or intravenously administrated, but do so by different mechanisms depending on the route and protocol of administration.

The results of these experiments show that there are basic differences in the mechanism of suppression of EAE between orally and parenterally (e.g. intravenously) administered MBP. The results suggest that orally administered antigen acts predominantly via the generation of active suppression, whereas parenterally administered antigen acts via clonal anergy. Specifically supporting this conclusion is the inability of spleen cells from IV tolerized animals to suppress adoptively-transferred EAE. Additionally, different fragments of MBP were more or less effective in suppression with the different routes of administration. (see, for example, FIG. 7) The present findings may be used to advantage in designing immunosuppressive methods based on antigen-driven tolerance, such as the method of the present invention.

EXAMPLE 3

FINE-TUNING OF THE DETERMINATION OF THE IMMUNODOMINANT EPITOPE OF HUMAN MBP IN HUMANS BY ASSESSING ABILITY OF OVERLAPPING PEPTIDES TO STIMULATE MBP SPECIFIC T-CELL CLONES

Figure 8A:
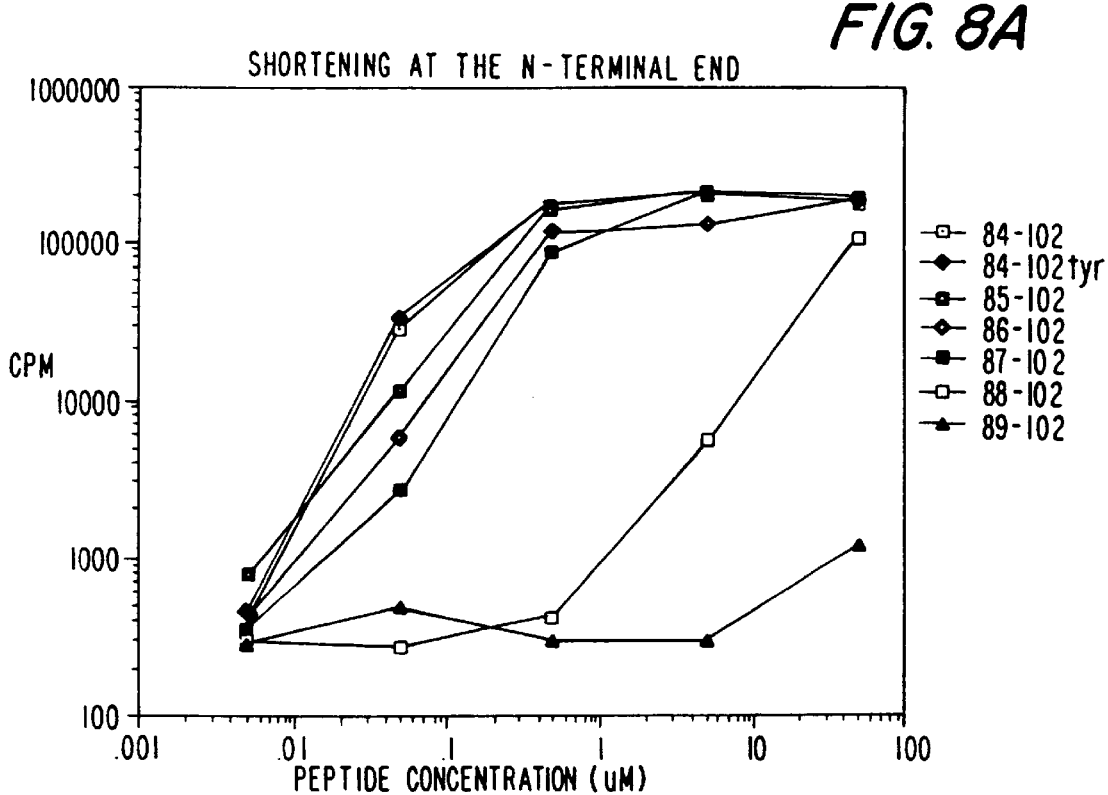
FIG. 8 is a graphic representation of the ability of various peptides constructed based on the immunodominant epitope region of human MBP (human MBP amino acid residues Nos. 84–102) to stimulate proliferation of human MBP-reactive T-cell clones. Panel A (FIG. 8A): effect of omitting one or more N-terminal amino acids; Panel B (FIG. 8B): effect of omitting one or more C-terminal amino acids.
Figure 8B:
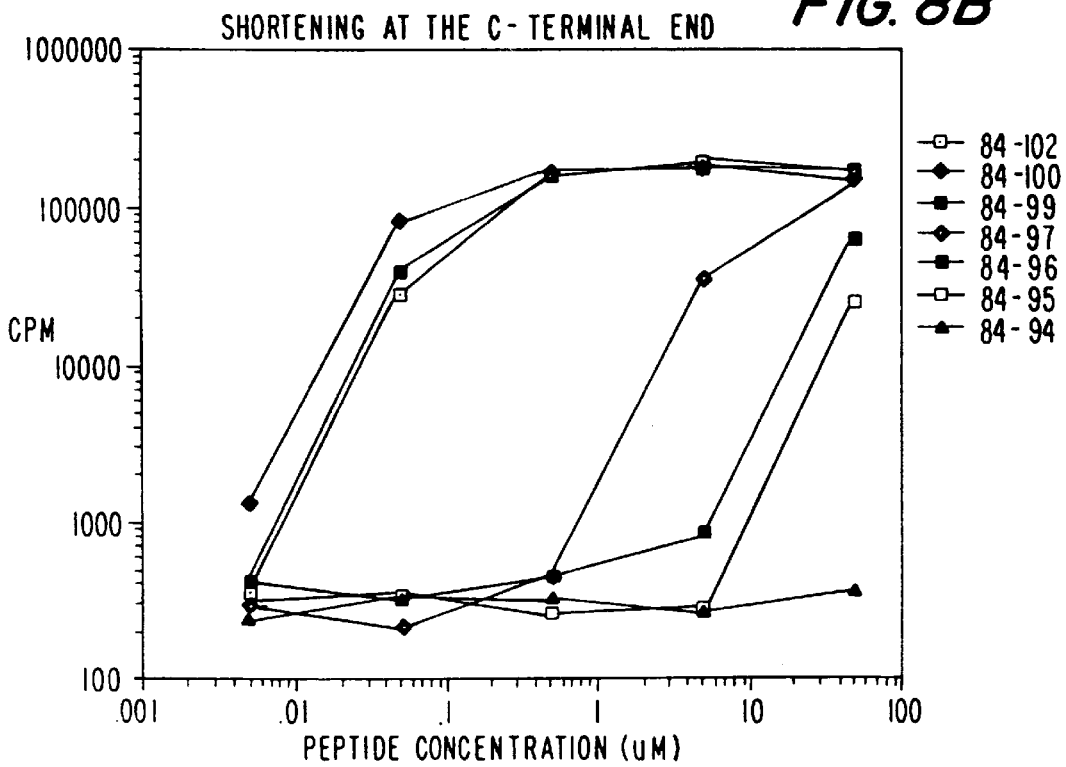
Figure 9A:
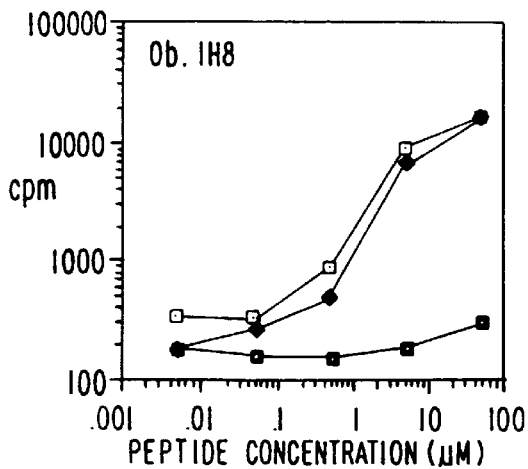
FIG. 9 is a graph of the ability of a 15-mer (human MBP amino acid residue Nos. 85–99) to stimulate proliferation of four different human T-cell clones (FIGS. 9A, 9B, 9C, 9D) compared to the ability of MBP peptides 84–102 and 86–97 to stimulate such proliferation.
Figure 9B:
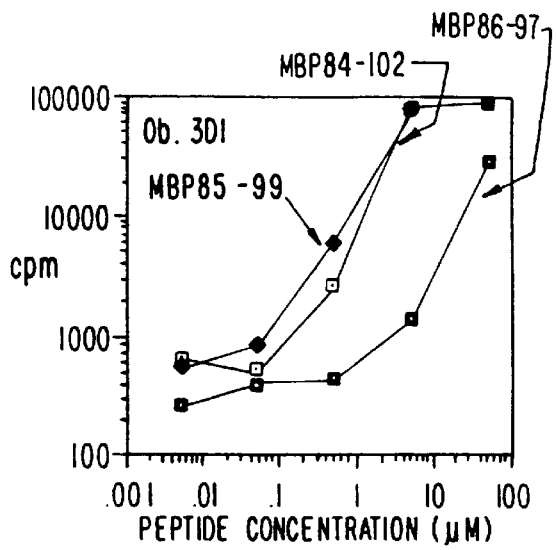
Figure 9C:
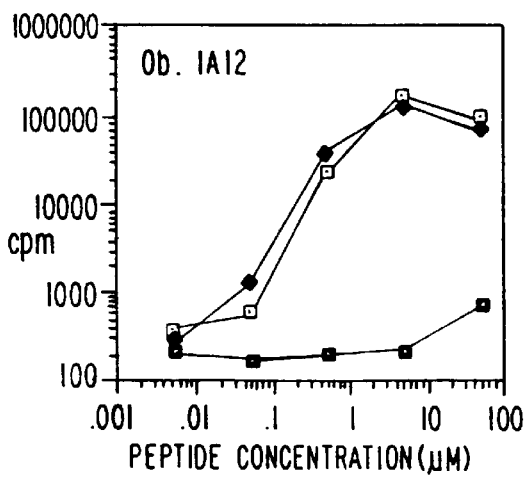
Figure 9D:
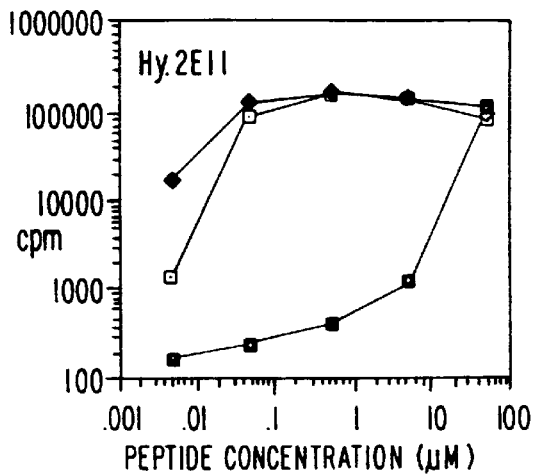

Using the cell proliferation assay described in Example 1 above, the ability of a peptide consisting of the immunodominant domain of human MBP (i.e. the sequence of amino acids 84–102) to stimulate T-cell proliferation was assessed and compared to that of a series of peptides having amino acid sequences representing N-terminal and C-terminal progressive truncations of the immunodominant domain was determined. As shown in FIG. 8, (and Table 5 below) the tested T-cell lines proliferated with a N-terminal truncation down to amino acid 85, after which there was a dramatic decrease in ability of the fragment to activate proliferation. Progressive C-terminal truncation quickly drastically affects stimulation ability, where truncation to only residue 99 does not substantially affect epitope function. In absence of C-terminal truncation, as shown in FIG. 8, loss of amino acids 85 and 86 also appear to be tolerated by the tested clone. In FIG. 9, four different T-cell clones were exposed to whole MBP 84–102 peptide and to peptides 85–99 and 86–97 to test whether different peptides caused differences in proliferation of the different clones. Although individual clones have inherently different abilities to proliferate in the presence of an epitopic peptide, nevertheless, the ability of a particular peptide to cause a clone to proliferate is qualitatively similar from clone to clone. From these studies it appears that the fragment amino acids 85–99 would comprise a minimal immunodominant fragment able to stimulate T-cell activity for all T-cell clones.

Table 5, below lists the ability of human MBP (84–102) specific T-cell clones to proliferate in the presence of MBP (84–102) peptide and truncated or modified versions of this peptide. The numbers in the matrix are peptide concentrations (expressed in micromolar) that give 50% maximal stimulation of the T-cell clones. Maximal stimulation of the T-cell clones was assessed by exposing them to unmodified untruncated MBP (84–102) peptide. The bold face designates "50" and ">50" mean a five-fold or more than a five-fold loss in stimulative activity compared to the untruncated unmodified MBP (84–102) peptide.

(84–102) peptide to autoreactive T-cells. APC's were pulsed with the MPB (84–102) peptide (100 µg/ml) for B-cell lines and 50 µg/ml for DR transfectants, irradiated with 5000 rad and co-cultured with the T-cell clones for three days followed by a thymidine pulse. The results ($^3$H-thymidine uptake compared to native peptide) are expressed in black rectangles (90% of the maximum stimulation) grey with crosses (>50% of the maximum stimulation) light grey (>10% of the maximum stimulation) and white (no activity). The results show that the Val at position 898 and the Phe at position 92 are involved in MHC binding. Truncation data suggest that the isoleucine at position 95 is also involved in MHC binding. T-cell receptor contact points include His at 90, Phe at 91 and Lys at 93.

Figure 10:
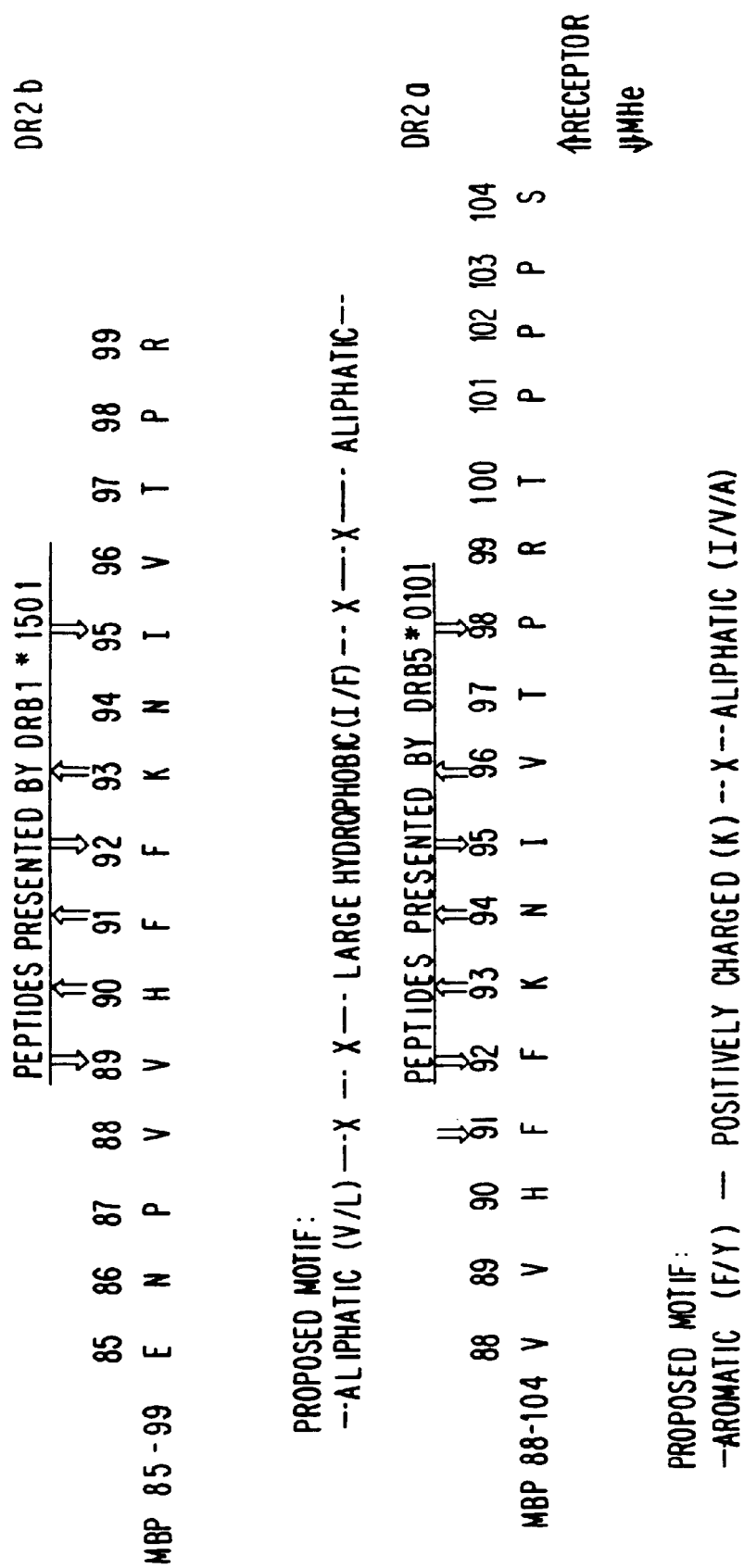
FIG. 10 is a chart showing the TCR/MHC contacts for the 85–99 and 88–104 human MBP peptides and a proposed motif for this interaction.

T-cell clone Hy.2Ell will tolerate an Arg substitution in place of Lys at 93 but the Ob T-cell clones will not. The proposed binding motifs for DRB1*1501 and DRB5*0101 are in FIG. 10. The arrows up indicate binding to the DR receptor and the arrows down indicate binding to the MHC of APC.

A series of analog peptides will be synthesized to both conservative and non-conservative amino acid substitutions at positions 88–95 that will be used. For example, the negative charge aspartic acid will be substituted with another negatively charged residue (glutomic acid), an amino acid with the same bulk but no charge (asparginine), an amino acid with the opposite charge (lys), and lastly a small amino acid such as ala. Proximately 60 peptides will need to be synthesized.

Preliminary data suggest that the 148–162 region of MBP is the minimal epitope for dominant epitope 143–168. When the core region of this peptide is defined using the methods outlined in Examples 2 and 3, a similar analysis as outlined in this Example 4 for MBP peptides 85–99.

Analog peptides will be analyzed for DR26-(DRB1*1501), DR2a-(DRB5*0101), DR4, DR7, and

TABLE 5

Comparison of the Relative Efficiency of Truncated Peptides to Stimulate MBP (84–102) Specific T cell clones

|        | Ob.1H8 | Ob.1E10 | Ob.2G9 | Ob.1C3 | Ob.1A12 | Ob.2F3 | Ob.3D1 | Hy.2E11 |
|--------|--------|---------|--------|--------|---------|--------|--------|---------|
| 84–102 | 3.1    | 4.0     | 3.8    | 2.9    | 1.6     | 2.1    | 2.0    | 0.26    |
| 84–102 | 2.0    | 3.1     | 3.2    | 2.9    | 1.6     | 1.5    | 2.0    | 0.26    |
| 85–102 | 12     | 1.8     | 3.6    | 4.0    | 0.4     | 1.5    | 2.0    | 0.31    |
| 86–102 | >50*   | >50     | >50    | 50     | 4.8     | 17     | 2.0    | 0.45    |
| 87–102 |        |         |        | >50    | >50     | >50    | 4.2    | 0.80    |
| 88–102 |        |         |        |        |         |        | >50    | 50      |
| 89–102 |        |         |        |        |         |        |        | >50     |
| 84–100 | 2.2    | 1.8     | 1.2    | 2.2    | 0.65    | 1.9    | 2.5    | 0.08    |
| 84–99  | 3.1    | 4.0     | 2.1    | 2.3    | 1.6     | 2.1    | 2.2    | 0.26    |
| 84–97  | >50    | >50     | >50    | >50    | 22      | 22     | 11     | 25      |
| 84–96  |        |         |        |        | >50     | >50    | 50     | >50     |
| 84–95  |        |         |        |        |         |        | >50    |         |

Peptide concentrations (µM) that give 50% maximal stimulation (reference point: MBP(84–102) peptide) are given. *More than a fivefold loss in activity compared to the MBP(84–102) peptide.

EXAMPLE 4

T-CELL RECOGNITION OF THE ALANINE ANALOG PEPTIDES OF MBP 85–99-REACTIVE T-CELL CLONES

FIG. 11 shows the binding of each peptide to MHC (left column) and to a T-cell clone (right panel). DRB1*1501 transfected L cells present the immunodominant MBP DQ1.1 binding. This analysis will elucidate further which amino acid residues are involved in MHC binding. Analog peptides that have no less than 10-times the binding capacity of the native peptide will be used to examine T-cell receptor specificity.

The present invention has been illustrated by reference to specific Examples. It will be apparent to those of ordinary skill, however, that many additions, deletions and modifications are possible without departing from the spirit or scope of the invention as claimed.

What is claimed is:
1. A method for suppressing immune function of CD4+ T-cells reactive with myelin basic protein in a human afflicted with multiple sclerosis comprising administering to said human via the intravenous route a peptide, the amino acid sequence of which is all or a segment of the sequence SLPQKSHGRTQDENPVVHFFKNIVTPRT-PPPSQGKGRGLS provided that said sequence comprises a portion of DENPVVHFFKNIVTPRTPP sufficient to impart to said peptide the property of stimulating, as determined by proliferation assay, the subgroup of HLA-DR2b restricted T-cell clones from remitting-relapsing multiple sclerosis patients that is reactive with another peptide the sequence of which consists of DENPVVHFFKNIVTPRTPP, said peptide stimulating said subgroup of T-cells to about the same degree as said another peptide.

2. A method for suppressing autoimmune response in a human suffering from multiple sclerosis, the method comprising orally administering to said human a peptide, the amino acid sequence of which is all or a segment of the sequence LPQKSHGRTQDENPVVHFFKNIVTPRTP-PPSQGKGRGLS provided that said sequence comprises a portion of DENPVVHFFKNIVTPRTPP sufficient to impart to said peptide has the property of stimulating, as determined by proliferation assay, the subgroup of HLA-DR2b restricted T-cell clones from remitting-relapsing multiple sclerosis patients that is reactive with another peptide, the sequence of which consists of DENPVVHFFKNIVTPRTPP, said peptide stimulating said subgroup of T-cells to about the same degree as said another peptide.

3. The method of claim 1 wherein said peptide is administered in an amount within the range of 1 to 200 mg.

4. The method of claim 2 wherein said peptide is administered in an amount within the range of 10 μg to 200 mg of said peptide.

5. The method of claim wherein the sequence of said peptide is DENPVVHFFKNIVTPRTPP.

* * * * *

UNITED STATES PATENT AND TRADEMARK OFFICE
CERTIFICATE OF CORRECTION

PATENT NO. : 6,036,957
DATED : March 14, 2000
INVENTOR(S) : WEINER et al.

It is certified that error appears in the above-identified patent and that said Letters Patent is hereby corrected as shown below:

In Col. 26, claim 5, change "The method of claim wherein the sequence of said peptide is DENPVVHFFKNIVTPRTPP" to --The method of claim 1 wherein the sequence of said peptide is DENPVVHFFKNIVTPRTPP--.

Signed and Sealed this

Fifth Day of June, 2001

*Attest:*

*Attesting Officer*

NICHOLAS P. GODICI

*Acting Director of the United States Patent and Trademark Office*